(12) United States Patent
Aimone et al.

(10) Patent No.: US 7,018,999 B2
(45) Date of Patent: Mar. 28, 2006

(54) METHODS FOR THE TREATMENT AND PREVENTION OF PAIN

(75) Inventors: Lisa D. Aimone, Reading, PA (US); Robert L. Hudkins, Chester Springs, PA (US); Matthew S. Miller, Solomons, MD (US)

(73) Assignee: Cephalon, Inc., Frazer, PA (US)

( * ) Notice: Subject to any disclaimer, the term of this patent is extended or adjusted under 35 U.S.C. 154(b) by 402 days.

(21) Appl. No.: 10/146,680

(22) Filed: May 15, 2002

(65) Prior Publication Data

US 2003/0087899 A1 May 8, 2003

Related U.S. Application Data

(60) Provisional application No. 60/291,227, filed on May 16, 2001.

(51) Int. Cl.
*A61K 31/54* (2006.01)

(52) U.S. Cl. ............... 514/224.5; 514/229.2; 514/249; 514/211; 540/445

(58) Field of Classification Search .............. 514/224.5, 514/229.2, 249, 211; 540/445
See application file for complete search history.

(56) References Cited

U.S. PATENT DOCUMENTS

| | | | |
|---|---|---|---|
| 1,381,031 | A | 6/1921 | Thompson |
| 4,877,776 | A | 10/1989 | Murakata et al. |
| 4,923,986 | A | 5/1990 | Murakata et al. |
| 5,093,330 | A | 3/1992 | Caravatti et al. |
| 5,468,872 | A | 11/1995 | Glicksman et al. |
| 5,516,771 | A | 5/1996 | Dionne et al. |
| 5,534,426 | A | 7/1996 | Karin et al. |
| 5,593,884 | A | 1/1997 | Karin et al. |
| 5,594,009 | A | 1/1997 | Hudkins et al. |

(Continued)

FOREIGN PATENT DOCUMENTS

| | | |
|---|---|---|
| GB | 2 337 702 | 12/1999 |
| WO | WO 93/08809 | 5/1993 |
| WO | WO 95/03324 | 2/1995 |
| WO | WO 97/49406 | 12/1997 |
| WO | WO 99/53927 | 10/1999 |
| WO | WO 99/58982 | 11/1999 |
| WO | WO 00/06563 | 2/2000 |

(Continued)

OTHER PUBLICATIONS

Glicksman et al., CEP–1347/KT7515 Prevents Motor Neuronal Programmed Cell Death and Injury–Induced Dedifferentiation In Vivo, J. Neurobiol. 35, 361–378, 1998.*
Borasio et al., CEP–1347/KT7515, a JNK partway inhibitor, supports the in vivo survival of chick embryonic neurons, NeuroReport 9, 1435–1439, 1998.*
Saporito et al., CEP–1347/KT–7514, an Inhibitor of c–jun N–Terminal Kinase Activation, The American Society for Pharmacology and Experimental Therapeutics, TPET 288: 421–427, 1999.*
Wagner et al., CEP–1374 Inhibits Caerulein–Induced Rat Pancreatic JNK Actiation and Ameliorates Caerulein Pancreatitis, Am. J. Physiol. Gastrointest. Liver Physiol. 278: G165–G172, 2000.*
Bennet et al., "SP600125, a selective inhibitor of JNK that modulates the activation and differentiation of CD4+ cells", Inflammation Research, vol. 49, No. Supplement 2, 2000, p. S102 (abstract).
Bodner et al., "CEP–1347/KT7515 rescues rat dorsal root ganglia from gp 120IIIB–induced apoptosis", Society for Neuroscience Abstracts, vol. 26, No. 1–2, 2000 (abstract).
Clerk et al., "The p38–MAPK inhibitor, SB203580 inhibits cardiac stress–activated protein kinases/c–Jun N–terminal kinases (SAPKs/JNKs)", FEBS Letters, Elsevier Science Publishers, Ambsterdam, NL, vl. 426, No. 1, 1998, pp. 93–96.
Forrer et al., "Enzyme–linked immunosorbent assay for measurement of JNK, ERK<and p38 kinase activities", Biological Chemistry, vol. 379, No. 8–9, 1998, pp. 1101–1111.
Beers, M.H., *The Merck Manual of Diagnosis & Therapy*, 1999, Merck Research Laboratories, New York, USA, XP002214785, p. 1491, col. 2, paragraph 5; p. 1496, col. 2, paragraph 3.
Brenner, B. et al., *The Journal of Biological Chemistry*, 1997, 272(35), 22173–22181.
Chapman, C.R. et al., *Pain*, 1990, 43, 47–55.
Galer, B.S. et al, *Pain*, 1992, 49, 87–91.
Guan, Z. et al., *The Journal of Biological Chemistry*, 1997, 272(12), 8083–8089.
Hai, T. et al., *Gene Expression*, 1999, 7, 321–335.
Kramer, R.M. et al., *The Journal of Biological Chemistry*, 1996, 271(44), 27723–27729.
Kyriakis, J.M. et al., *BioEssays*, 1996, 18(7), 567–577.
Lin, L. et al., *Cell*, 1993, 72, 269–278.
Maroney, A.C., et al., *The Journal of Neuroscience*, 1998, 18(1), 104–111.
Nakanishi, O. et al., *Cellular and Molecular Neurobiology*, 1999, 19(2), 191–197.
Portenoy, R.K. et al., *Pain*, 1990, 43, 273–286.
Xia, Z. et al., *Science*, 1995, 270, 1326–1331.
Xie, W. et al., *The Journal of Biological Chemistry*, 1995, 270(46), 27622–27628.
Xie, W. et al., *Molecular and Cellular Biology*, 1994, 14(10), 6531–6539.

*Primary Examiner*—Johnn Richter
*Assistant Examiner*—Chukwuma Nwaonicha
(74) *Attorney, Agent, or Firm*—Scott K. Larsen; Robert T. Hrubiec

(57) ABSTRACT

Novel methods for the treatment and/or prevention of pain are presented. The methods may comprise administering to a subject in need thereof an effective amount of a stress-activated protein kinase inhibitor. Preferred compounds for use in the methods include fused pyrrolocarbazole compounds.

17 Claims, 7 Drawing Sheets

U.S. PATENT DOCUMENTS

| | | |
|---|---|---|
| 5,599,808 A | 2/1997 | Goldstein et al. |
| 5,605,808 A | 2/1997 | Karin et al. |
| 5,616,724 A | 4/1997 | Hudkins et al. |
| 5,621,101 A | 4/1997 | Lewis et al. |
| 5,705,511 A | 1/1998 | Hudkins et al. |
| 5,756,494 A | 5/1998 | Lewis et al. |
| 6,046,208 A | 4/2000 | Adams et al. |
| 6,093,713 A | 7/2000 | Hudkins et al. |
| 6,127,401 A | 10/2000 | Singh et al. |
| 6,306,849 B1 | 10/2001 | Hudkins et al. |
| 6,399,780 B1 | 6/2002 | Hudkins |

FOREIGN PATENT DOCUMENTS

| | | |
|---|---|---|
| WO | WO 00/13015 | 3/2000 |
| WO | WO 00/35906 | 6/2000 |
| WO | WO 00/35909 | 6/2000 |
| WO | WO 00/35921 | 6/2000 |
| WO | WO 00/47583 | 8/2000 |
| WO | WO 00/64872 | 11/2000 |
| WO | WO 00/75118 | 12/2000 |
| WO | WO 01/01986 | 1/2001 |
| WO | WO 01/05390 | 1/2001 |
| WO | WO 01/12609 | 2/2001 |
| WO | WO 01/12621 | 2/2001 |
| WO | WO 01/14380 | 3/2001 |
| WO | WO 01/91749 | 12/2001 |
| WO | WO 02/38035 | 5/2002 |
| WO | WO 02/46184 | 6/2002 |

\* cited by examiner

Figure 1. Flinching/Shaking – 24 Hour Pretreatment
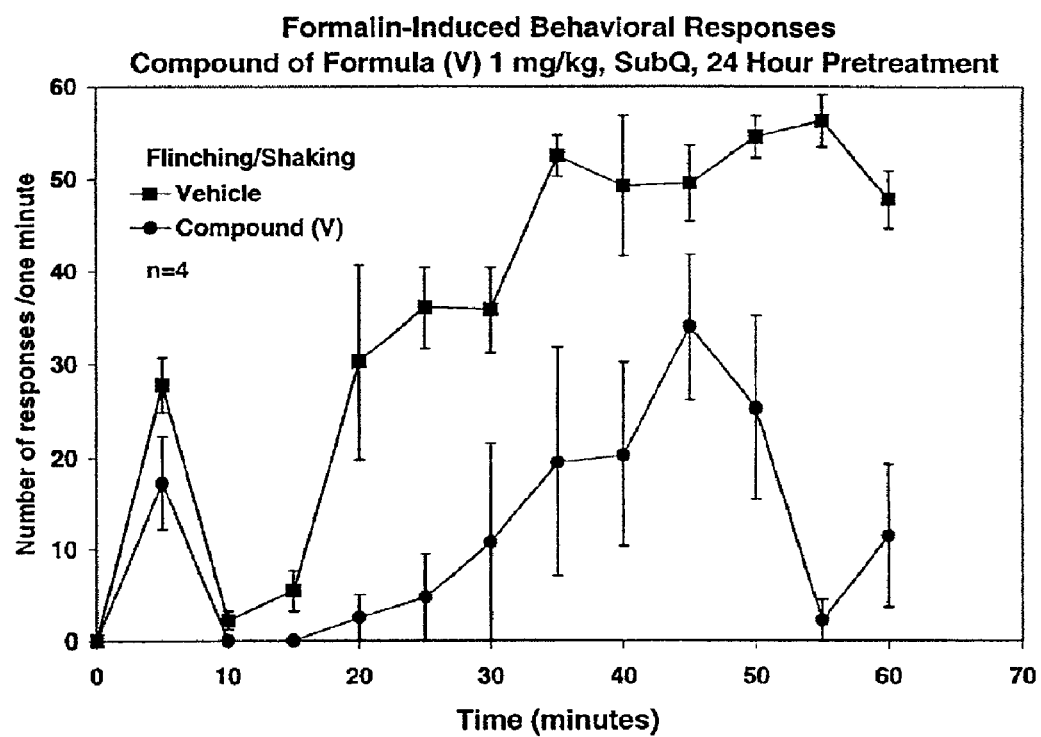

Figure 2. Licking/Biting – 24 Hour Pretreatment
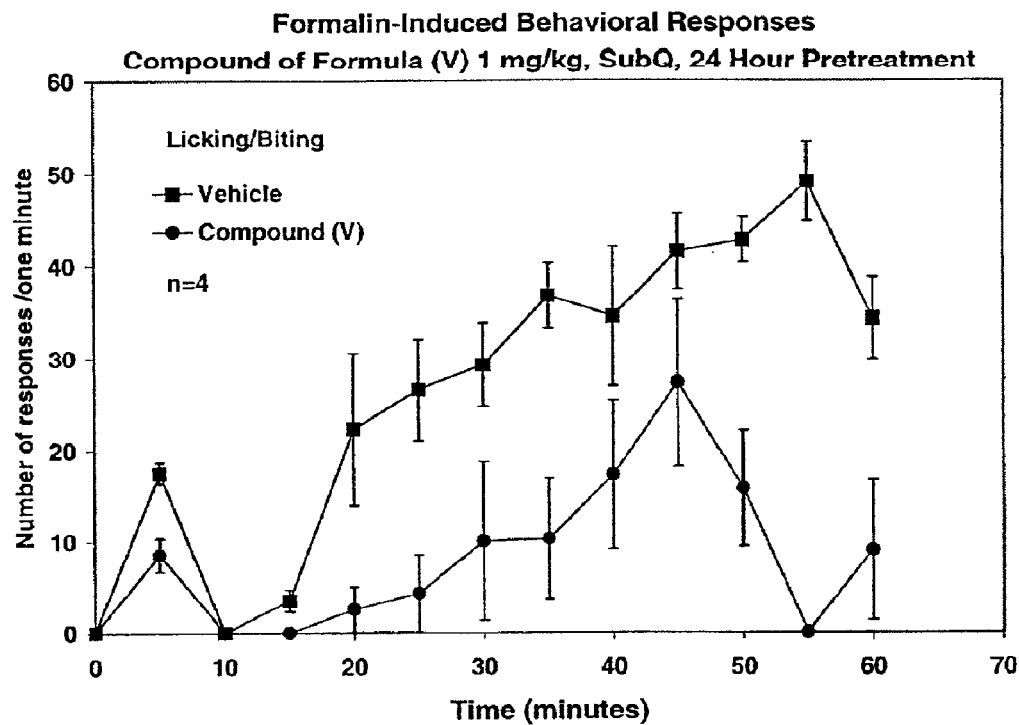
Figure 3. Flinching/Shaking repeat
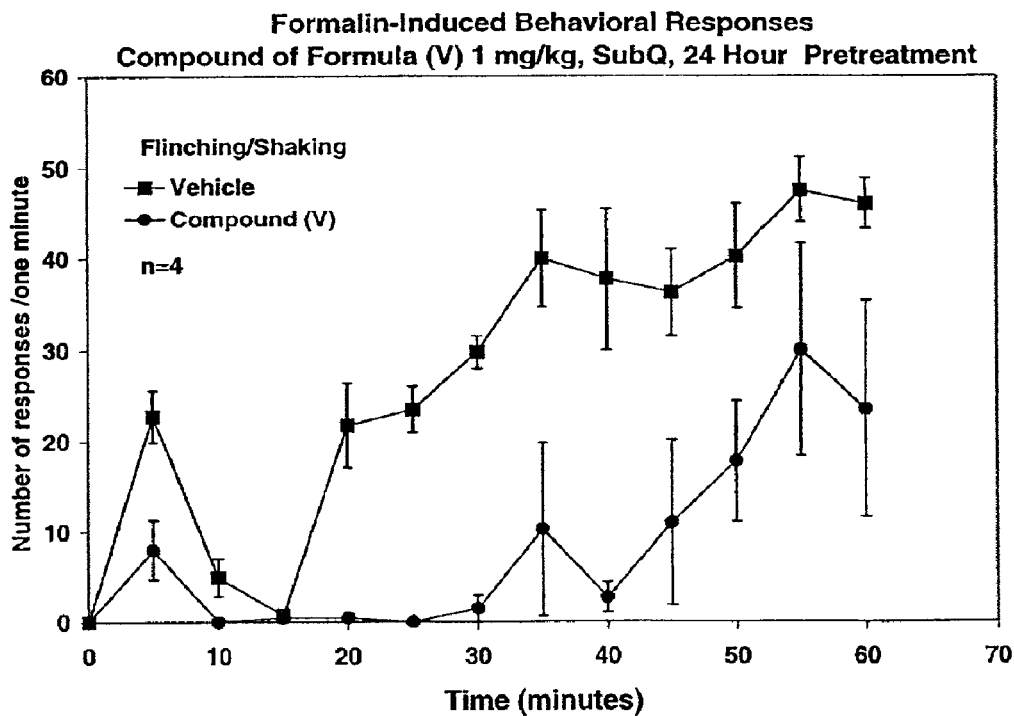

Figure 4. Licking/Biting repeat
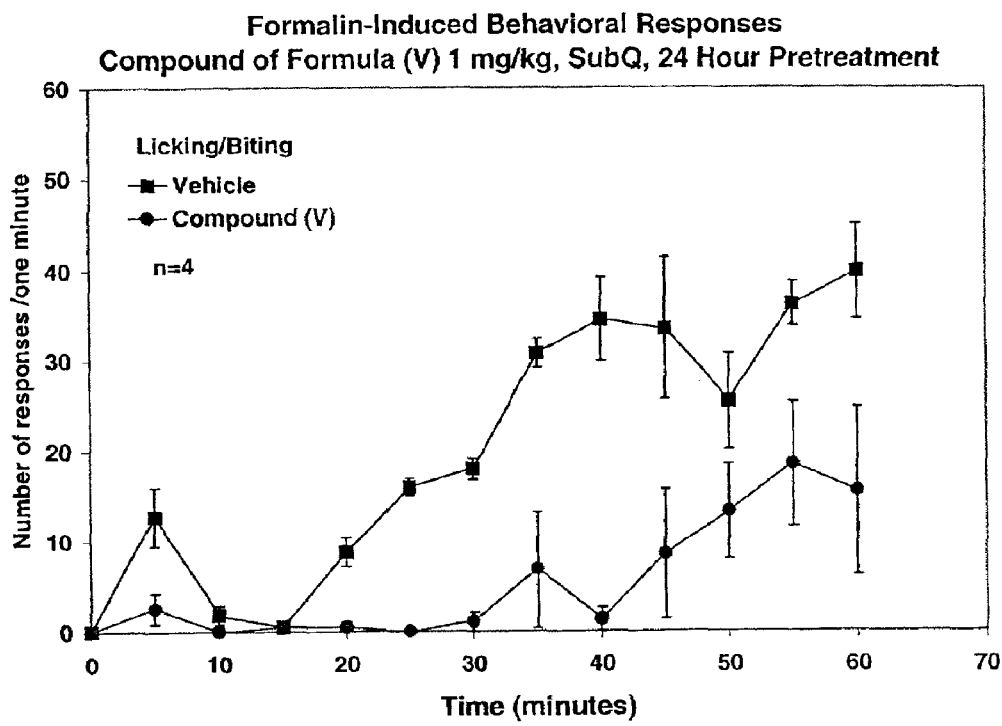
Figure 5. Flinching/Shaking – Two Hour Pretreatment
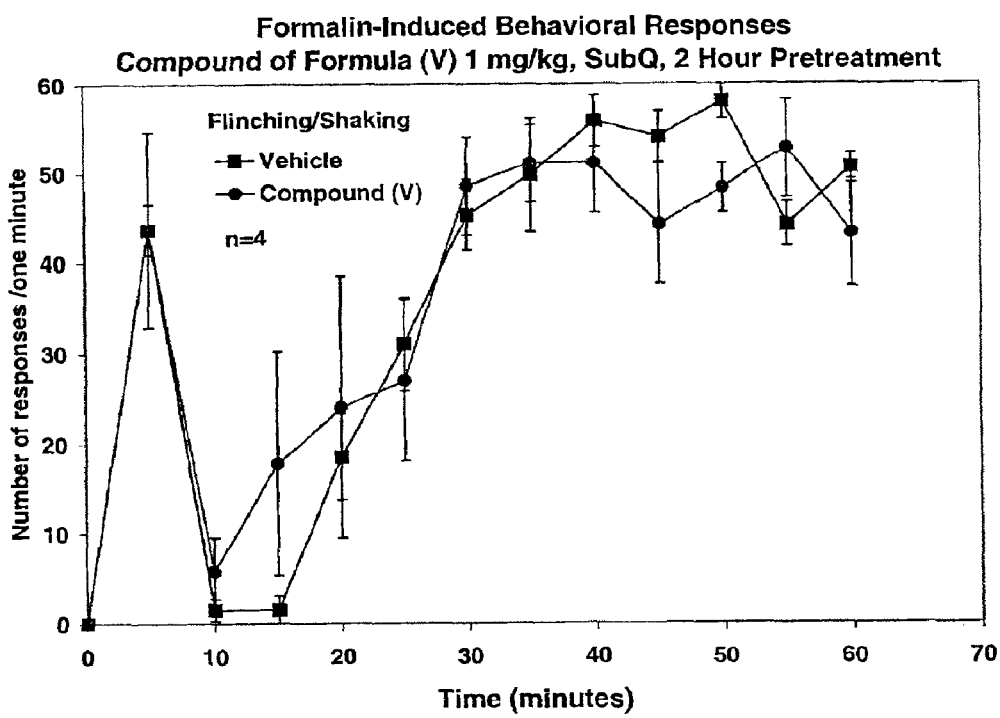

Figure 6. Licking/Biting – Two Hour Pretreatment
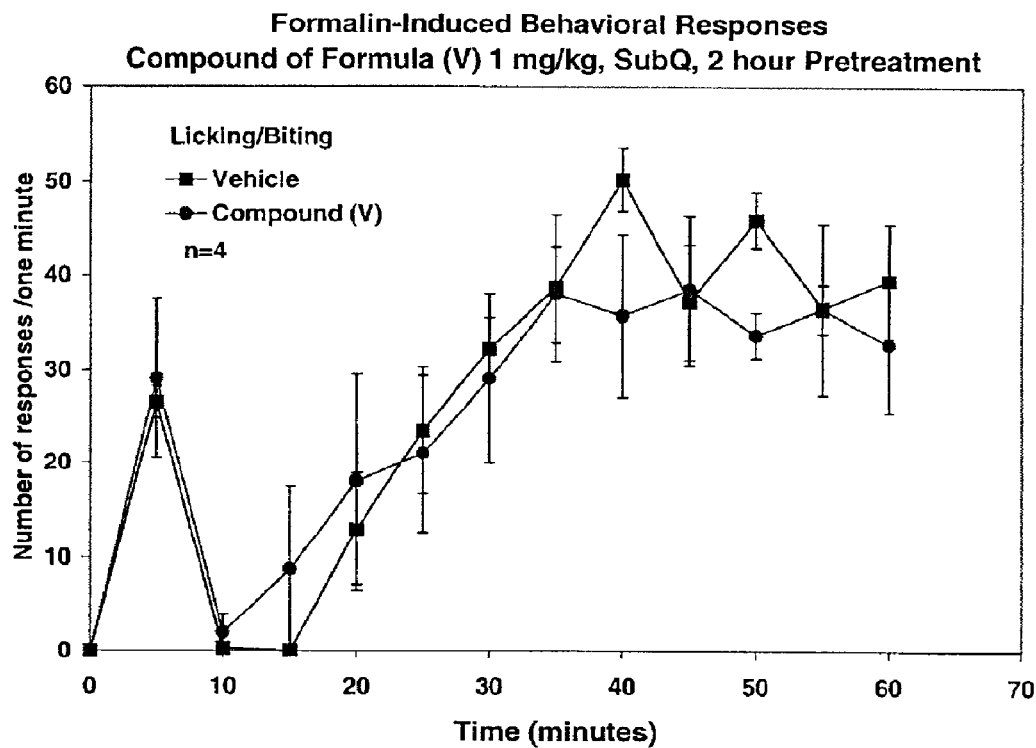
Figure 7. Dose Response - Flinching/Shaking
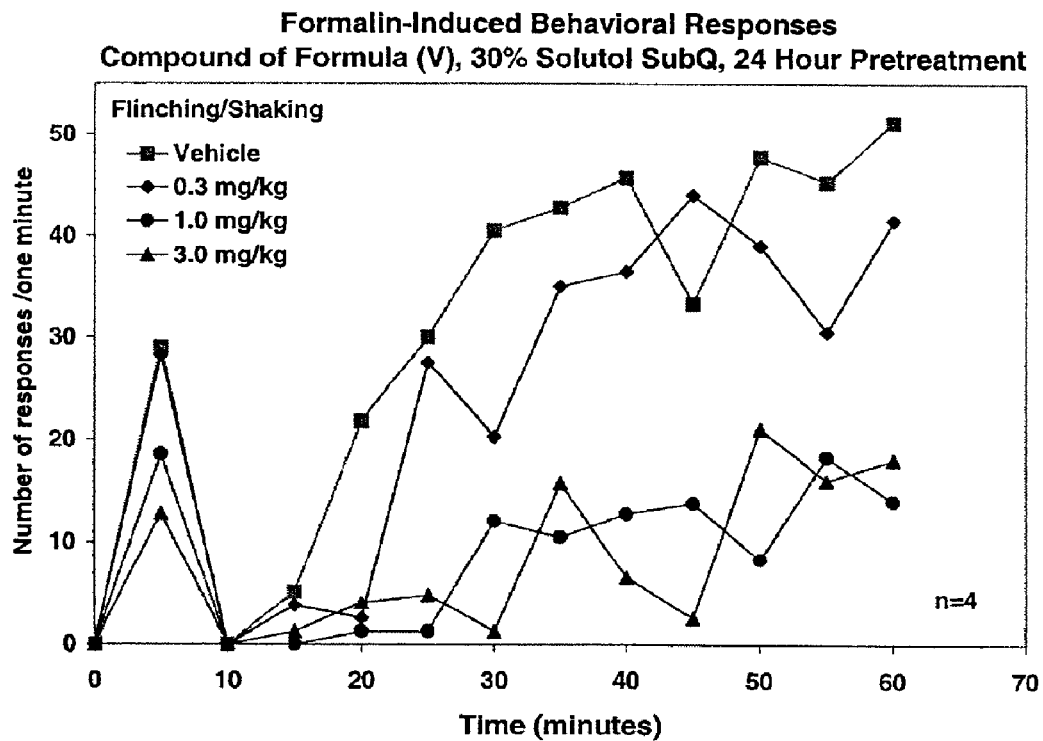

Figure 8. Dose Response – Licking/Biting
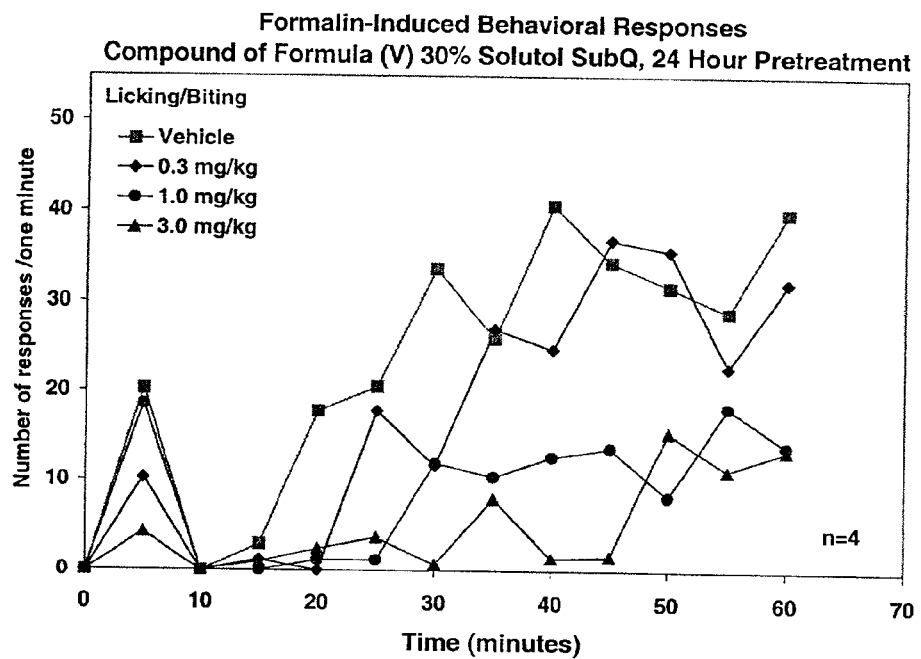
Figure 9. Hindpaw Inflammation after Formalin Injection
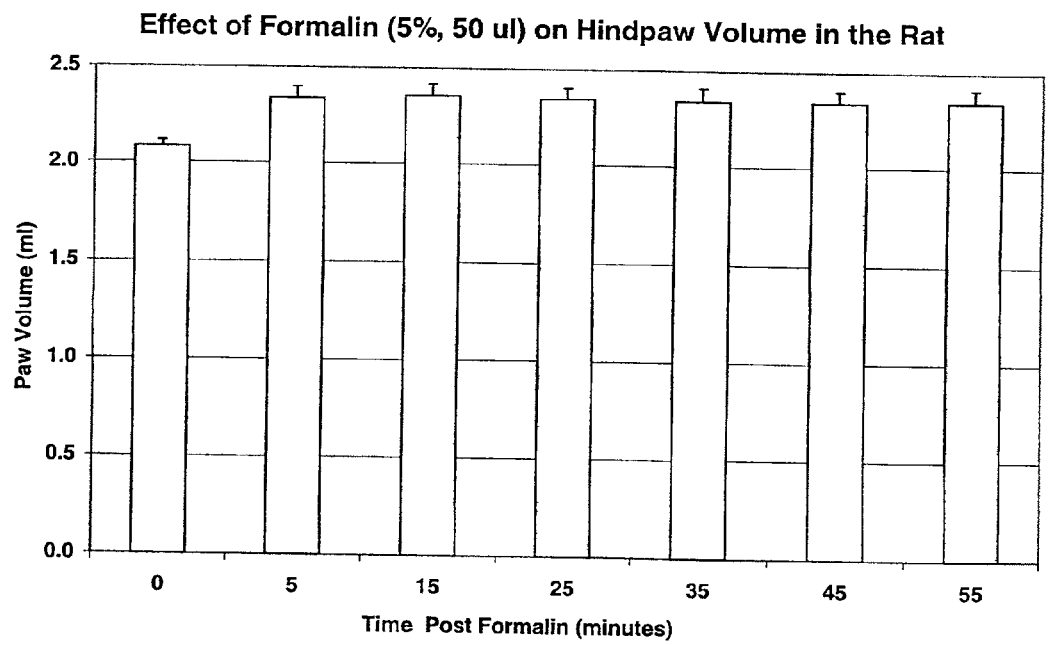

Figure 12. Graphical Representation of Phase II
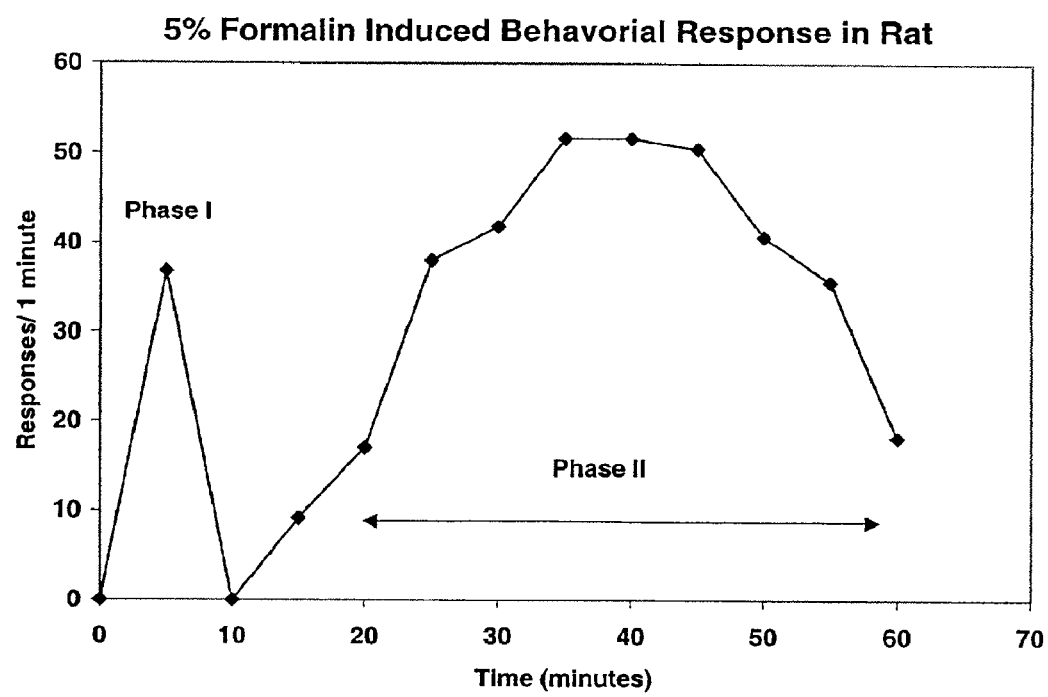

METHODS FOR THE TREATMENT AND PREVENTION OF PAIN

CROSS-REFERENCE TO RELATED APPLICATIONS

This application claims the benefit of prior filed, copending U.S. provisional application 60/291,227, filed May 16, 2001, the disclosure of which is incorporated herein by reference in its entirety.

FIELD OF THE INVENTION

The present invention relates to novel methods for the treatment and prevention of pain. More particularly, the present invention relates to novel methods for the treatment and prevention of pain by using stress-activated protein kinase inhibitors.

BACKGROUND OF THE INVENTION

The stress-activated protein kinases (SAPKs), also referred to as c-jun-$NH_2$-terminal kinases (JNKs), comprise a subfamily of proteins which belongs to the mitogen-activated protein kinase (MAPK) group of protein kinases. The MAPK pathways have been implicated as a mechanism by which signals are transduced from the cell surface to the nucleus in response to a variety of different stimuli and participate in intracellular processes by further inducing the phosphorylation of intracellular substrates such as other protein kinases and transcription factors.

The SAPK family includes, in part, p54 SAPKα/β/JNK2 and p45 SAPKγ/JNK1 and the p38 MAPKs (α,β, βII, γ, and δ). Guan, et al., *J. Biol. Chem.*, 1998, 273, 28670–28676. JNK is described in U.S. Pat. Nos. 5,534,426, 5,593,884 and 5,605,808, and WO 95/03324. It has been reported previously that the inflammatory cytokine interleukin-1β (IL-1β) rapidly activates the JNK/SAPKs and p38 MAPKs and also induces cyclooxygenase-2 (COX-2) expression and prostaglandin $E_2$ ($PGE_2$) production. Guan et al., *J. Biol. Chem.*, 1997, 272, 8083–8089. Interestingly, it has been suggested that the MAPK pathway is also involved in regulating prostaglandin biosynthesis. Lin et al., *Cell*, 1993, 72, 269–278; Kramer et al., *J. Biol. Chem.*, 1996, 271, 27723–27729. The requirement of JNK/SAPK activity for cytokine-induced prostaglandin biosynthesis, has also been reported. Xie et al., *J. Biol. Chem.*, 1995, 270, 27622–27628; Xie et al., *Mol. Cell. Biol.*, 1994, 14, 6531–6539.

The elucidation of all the aforementioned pathways, however, still remains unclear. Also, the sequence of events through which a signal induced by a noxious stimulus (UV irradiation, heat shock, X-ray, etc.) gets transmitted into the nucleus, and thus renders certain nuclear factors to act as oncogenes, or transcribe and activate other subsequent pathways, is vaguely understood. Recent work has implicated the JNK/SAPK pathway in connection with the induction of transcription factors as a response to stress signals, thereby demonstrating the importance of SAPKs in the activation of ATF3, a member of the ATF/CREB family of transcription factors. Hai, et al., *Gene Expression*, 1999, 7, 321–335. The JNK/SAPK pathway has been also implicated in cell proliferation and stress-induced programmed cell death (apoptosis). Kyriakis, et al., *BioEssays*, 1996, 18 567–577; Xia, et al., *Science*, 1995, 270, 1326–1331; Brenner, et al., *J. Biol. Chem.*, 1997, 272, 22173–22181.

Nonsteroidal anti-inflammatory drugs (NSAIDs) and opioids have been the most widely used pain killers for many years. In some circumstances, NSAIDs are able to provide better analgesia than opioids. The NSAIDs act by blocking the action of COX-2, which is the enzyme responsible for the conversion of arachidonic acid to prostaglandins. Taylor P. M., *Vet. Clin. North Am.*, 1999, 29 719–733. NSAIDs have been valuable tools in the elucidation of prostaglandin biosynthesis pathways, as well as providing a starting point for the rational design and synthesis of new anti-inflammatory drugs.

However, despite the wide use of both NSAID and opioid analgesics, current pain relievers often display large clinical (Galer et al., *Pain*, 1992, 49, 87–91; Portenoy et al., *Pain*, 1990, 43, 273–286) and experimental (Chapman et al., *Pain*, 1990, 43, 47–55) variability in their efficacies, side effects, and tolerance liability. This is probably because, at least in some areas, COX-2 also has a regulatory role in normal function. Thus, serious and undesirable effects such as toxicity, anemia and gastrointestinal lesions may be associated with the long-term use of NSAIDs. Opioids are generally known to cause nausea and vomiting as well as inhibition of normal propulsive gastrointestinal function in animals and man (Reisine, T., and Pasternak, G., *Goodman & Gilman's The Pharmacological Basis of Therapeutics Ninth Edition* 1996, 521–555) resulting in side effects such as, for example, nausea, vomiting and constipation.

Due to the drawbacks associated with currently available pain relivers, there exists a need for improved compositions and/or methods for the prevention and/or treatment of pain. The present invention is directed towards these, as well as other important ends.

SUMMARY OF THE INVENTION

It has been surprisingly and unexpectedly discovered that compounds which are inhibitors of stress-activated protein kinase (SAPK) may be advantageously used to treat and/or prevent pain. Therefore, in accordance with preferred embodiments, the methods of the present invention preferably comprise administering to a patient a SAPK inhibitor. Specifically, in one embodiment, there are provided methods of preventing or treating pain comprising administering to a subject in need thereof an effective amount of a compound having the following formula (I):

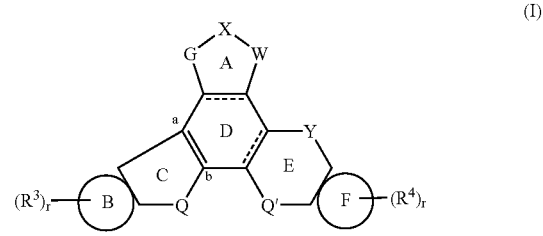

or a stereoisomer or pharmaceutically acceptable salt form thereof, wherein: A, B, C, D, E, F, G, W, X, Y, Q, Q', $R^3$, $R^4$, and r are defined below.

In other embodiments, the present invention provides a method of preventing or treating pain comprising administering to a subject in need thereof an effective amount of a compound having the following formula (VI):

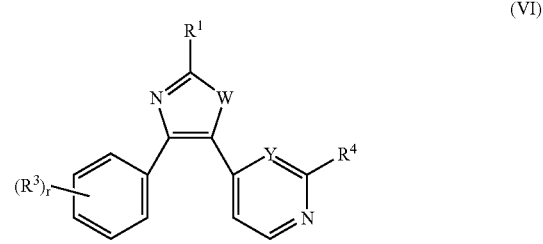

or a stereoisomer or pharmaceutically acceptable salt thereof, wherein W, Y, $R^1$ $R^3$, and $R^4$ are defined below.

In other embodiments, the present invention provides a method of preventing or treating pain comprising administering to a subject in need thereof an effective amount of a compound having the following formula (X):

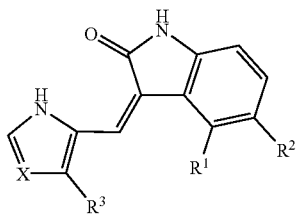

(X)

or a stereoisomer or pharmaceutically acceptable salt form thereof, wherein: X, $R^1$ $R^2$, and $R^3$ are defined below.

In other embodiments, the present invention provides a method of preventing or treating pain comprising administering to a subject in need thereof an effective amount of a compound having the following formula (XI):

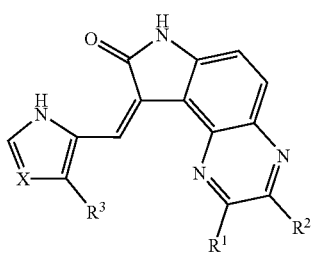

(XI)

or a stereoisomer or pharmaceutically acceptable salt form thereof, wherein: X, $R^1$, $R^2$, and $R^3$ are defined below.

In other embodiments, the present invention provides a method of preventing or treating pain comprising administering to a subject in need thereof an effective amount of a compound having the following formulas (XII) or (XIII):

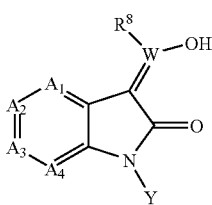

(XII)

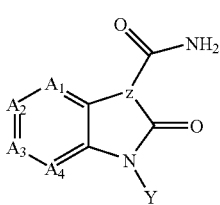

(XIII)

or a stereoisomer or pharmaceutically acceptable salt form thereof, wherein: $A_1$, $A_2$, $A_3$, $A_4$, W, Y, z, and $R^8$ are defined below.

In other embodiments, the present invention provides methods of preventing or treating pain comprising administering to a subject in need thereof an effective amount of a compound having formula (XIV):

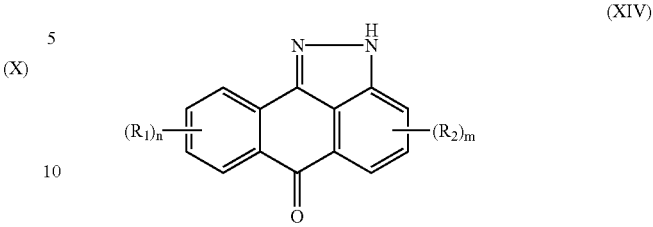

(XIV)

or a pharmaceutically acceptable salt thereof; wherein: $R_1$, $R_2$, n, and m are defined below.

In other embodiments, the present invention provides a method of treating or preventing pain comprising administering to a subject in need thereof an effective amount of a compound selected from stress-activated protein kinase inhibitors. In other embodiments, the compound inhibits a substrate involved in the stress-activated protein kinase pathway selected from JNK1, JNK2, and JNK3. In other embodiments, the compounds described herein are administered to the patient sufficiently prior to a painful stimulus to modulate, particularly, decrease, the painful event. In other embodiments, the invention relates to methods of preventing or treating pain wherein the pain is other than inflammatory pain. These and other aspects of the invention will become more apparent from the following detailed description.

BRIEF DESCRIPTION OF THE DRAWINGS

FIGS. 1 to 8 are graphical representations of studies on the inhibition of pain employing methods according to an embodiment of the present invention.

FIGS. 9 to 11 are graphical representations of studies on the modulation of anti-inflammatory activity by certain embodiments of the present invention.

FIG. 12 is a graphical representation of a 5% formalin-induced behavioral response.

DETAILED DESCRIPTION OF THE INVENTION

Figure 10:
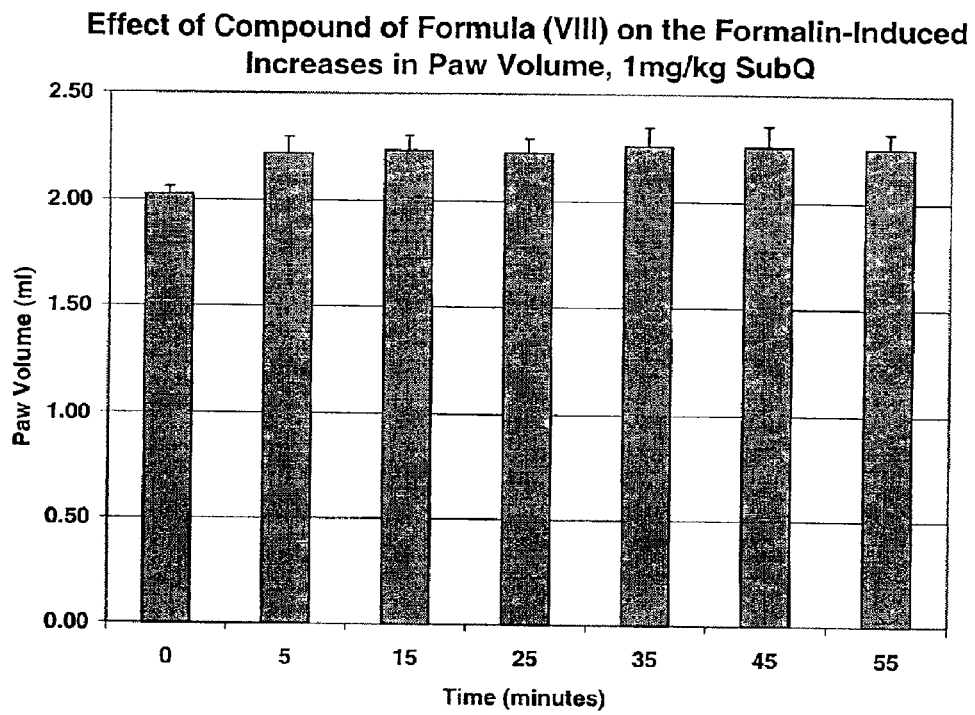

The present invention is directed, in part, to methods for the treatment and/or prevention of pain. Thus, in one embodiment, the present invention provides novel methods for treating and/or preventing pain. Specifically, in a first embodiment, there are provided methods of preventing or treating pain comprising administering to a subject in need thereof an effective amount of a compound having the following formula (I):

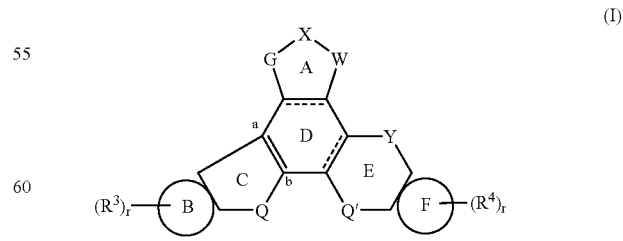

(I)

or a stereoisomer or pharmaceutically acceptable salt form thereof, wherein:
ring D is selected from phenyl and cyclohexene with double bond a-b;

ring B and ring F are independently selected from:
(a) a 6-membered aromatic ring in which from 1 to 3 carbon atoms may be replaced by heteroatoms;
(b) a 5-membered aromatic ring in which either:
  (1) one carbon atom is replaced with an oxygen, nitrogen, or sulfur atom;
  (2) two carbon atoms are replaced with a sulfur and a nitrogen atom, an oxygen and a nitrogen atom, or two nitrogen atoms; or
  (3) three carbon atoms are replaced with three nitrogen atoms, one oxygen and two nitrogen atoms, or one sulfur and two nitrogen atoms;

G-X-W is selected from:
(a) $(Z^1Z^2)C-N(R^1)-C(Z^1Z^2)$;
(b) $CH(R^1)-C(=O)-N(R^1)$; and
(c) $N(R^1)-C(=O)-CH(R^1)$;

$Z^1$ and $Z^2$, at each occurrence, are independently selected from H, H; H, OR; H, SR;

H, $N(R)_2$; and a group wherein $Z^1$ and $Z^2$ together form a moiety selected from =O, =S, and =NR; with the proviso that at least one of the pairs $Z^1$ and $Z^2$ forms =O;

R is independently selected from H, optionally substituted alkyl, $C(=O)R^{1a}$, $C(=O)NR^{1c}R^{1d}$, $(CH_2)_pNR^{1c}R^{1d}$, $(CH_2)_pOR^{1b}$, optionally substituted arylalkyl and optionally substituted heteroarylalkyl;

$R^1$ is independently selected from:
(a) H, optionally substituted alkyl, optionally substituted aryl, optionally substituted arylalkyl, optionally substituted heteroaryl and optionally substituted heteroarylalkyl;
(b) $C(=O)R^{1a}$;
(c) $OR^{1b}$;
(d) $C(=O)NHR^{1b}$, $NR^{1c}R^{1d}$, $(CH_2)_pNR^{1c}R^{1d}$, $(CH_2)_pOR^{1b}$, $O(CH_2)_pOR^{1b}$ and $O(CH_2)_pNR^{1c}R^{1d}$;

$R^{1a}$ is independently selected from optionally substituted alkyl, optionally substituted aryl and optionally substituted heteroaryl;

$R^{1b}$ is independently selected from H and optionally substituted alkyl;

$R^{1c}$ and $R^{1d}$ are each independently selected from H and optionally substituted alkyl, or together form linking group of the formula $(CH_2)_2-X^1-(CH_2)_2$;

$X^1$ is independently selected from O, S and $CH_2$;

Q is $NR^2$;

$R^2$ is selected from H, $SO_2R^{2e}$, $CO_2R^{2e}$, $C(=O)R^{2a}$, $C(=O)NR^{2c}R^{2d}$, optionally substituted alkyl, optionally substituted alkenyl and optionally substituted alkynyl, wherein said optional substituents are one to about three $R^5$ groups;

$R^{2a}$ is independently selected from optionally substituted alkyl, optionally substituted aryl, $OR^{2b}$, $CONH_2$, $NR^{2c}R^{2d}$, $(CH_2)_pNR^{2c}R^{2d}$ and $O(CH_2)_pNR^{2c}R^{2d}$;

$R^{2b}$ is selected from H and optionally substituted alkyl;

$R^{2c}$ and $R^{2d}$ are each independently selected from H and optionally substituted alkyl, or together form a linking group of the formula $(CH_2)_2-X^1-(CH_2)_2$;

$R^{2e}$ is selected from H, optionally substituted alkyl, optionally substituted aryl, $CONH_2$, $NR^{2c}R^{2d}$, and $(CH_2)_pNR^{2c}R^{2d}$;

$R^3$ and $R^4$ are each independently selected from:
(a) H, aryl, heteroaryl, F, Cl, Br, I, CN, $CF_3$, $NO_2$, OH, $OR^9$, $O(CH_2)_pNR^{11}R^{12}$, $OC(=O)R^9$, $OC(=O)$
$NR^{11}R^{12}$, $O(CH_2)_pOR^{10}$, $CH_2OR^{10}$, $NR^{11}R^{12}$, $NR^{10}S$
$(=O)_2R^9$ and $NR^{10}C(=O)R^9$;
(b) $CH_2OR^{14}$;
(c) $NR^{10}C(=O)NR^{11}R^{12}$, $CO_2R^{10}$, $C(=O)R^9$, $C(=O)$
$NR^{11}R^{12}$, $CH=NOR^{10}$, $CH=NR^{10}$, $(CH_2)_pNR^{11}R^{12}$, $(CH_2)_pNHR^{14}$ and $CH=NNR^{11}R^{12}$;
(d) $S(O)_yR^9$, $(CH_2)_pS(O)_yR^9$ and $CH_2S(O)_yR^{14}$;
(e) optionally substituted alkyl, optionally substituted alkenyl and optionally substituted alkynyl, wherein said optional substituents are one to about three $R^5$ groups;

$R^9$ is selected from alkyl, $(CH_2)_r$aryl and $(CH_2)_r$ heteroaryl;

$R^{10}$ is selected from H, alkyl, $(CH_2)_r$aryl and $(CH_2)_r$ heteroaryl;

$R^{11}$ and $R^{12}$ are independently selected from H and optionally substituted alkyl, or together form a linking group of the formula $(CH_2)_2-X^1-(CH_2)_2$;

$R^5$ is selected from aryl, heteroaryl, arylalkoxy, F, Cl, Br, I, CN, $NO_2$, OH, $OR^9$, $OC(=O)R^9$, $OC(=O)NHR^{10}$, O-tetrahydropyranyl, $NR^{11}R^{12}$, $NR^{10}C(=O)R^9$, $NR^{10}CO_2R^9$, $NR^{10}C(=O)NR^{11}R^{12}$, $NHC(=NH)NH_2$, $NR^{10}S(O)_2R^9$, $S(O)_yR^9$, $CO_2R^{10}$, $C(=O)NR^{11}R^{12}$, $C(=O)$
$R^9$, $CH_2OR^{10}$, $CH=NNR^{11}R^{12}$, $CH=NOR^{10}$, $CH=NR^9$, $CH=NNHCH(N=NH)NH_2$, $S(=O)_2NR^{11}R^{12}$, $P(=O)$
$(OR^{10})_2$, $OR^{14}$, and a monosaccharide wherein each hydroxyl group of the monosaccharide is independently either unsubstituted or is replaced by H, alkyl, alkylcarbonyloxy, or alkoxy;

Y is selected from:
(a) a direct bond;
(b) optionally substituted $CH_2$, $CH_2CH_2$ or $CH_2CH_2CH_2$, wherein said optional substituents are one to about three $R^{19}$ groups; and
(c) CH=CH, CH(OH)—CH(OH), O, S, S(=O),
$S(=O)_2$, $C(R^{18})_2$, $C=C(R^{19})_2$, $C(=O)$,
$C(=NOR^{20a})$, $C(OR^{20a})R^{20}$, $C(=O)CH(R^{18})$,
$CH(R^{18})C(=O)$, $C(=NOR^{20a})CH(R^{18})$, $CHR^{21}C$
$(=NOR^{20a})$, $C(=O)N(R^{21})$, $N(R^{21})C(=O)$, $CH_2Z$,
$ZCH_2$ and $CH_2ZCH_2$, where Z is selected from $C(R^{20})_2$, O, S, $CO_2R^{20a}$, $C(=NOR^{20a})$ and $N(R^{20})$;

$R^{18}$ is independently selected from H, $SO_2R^{18a}$, $CO_2R^{18a}$, $C(=O)R^{18a}$, $C(=O)NR^{18c}R^{18d}$, optionally substituted alkyl, optionally substituted alkenyl, and optionally substituted alkynyl;

$R^{18a}$ is independently selected from optionally substituted alkyl, optionally substituted aryl, optionally substituted carbocyclyl and optionally substituted heterocyclyl;

$R^{18c}$ and $R^{18d}$ are each independently selected from H and optionally substituted alkyl, or together form a linking group of the formula $(CH_2)_2-X^1-(CH_2)_2$;

$R^{19}$ is independently selected from $R^{20}$, thioalkyl, halogen, optionally substituted alkyl, optionally substituted alkenyl and optionally substituted alkynyl;

$R^{20}$ is independently selected from H, alkyl, OH, alkoxy, $OC(=O)R^{18a}$, $OC(=O)NR^{18c}R^{18d}$, $OC(=S)NR^{18c}R^{18d}$, $O(CH_2)_pNR^{18c}R^{18d}$, $O(CH_2)_pOR^{21}$, optionally substituted arylalkyl, optionally substituted heterocyclylalkyl and optionally substituted carbocyclyl;

$R^{20a}$ is independently selected from H, alkyl, optionally substituted arylalkyl, optionally substituted heterocyclylalkyl and optionally substituted carbocyclyl;

$R^{21}$ is independently selected from H and alkyl;

Q' is selected from a bond or:
(a) an optionally substituted $CH_2$, $CH_2CH_2$ or $CH_2CH_2CH_2$;
(b) $CR^{22}R^{24}$; and
(c) CH=CH, CH(OH)CH(OH), O, S, S(=O), S(=O)$_2$, C(=O), C(=NOR$^{11}$), C(OR$^{11}$)(R$^{12}$), C(=O)CH(R$^{13}$), CH(R$^{13}$)C(=O), C(R$^{10}$)$_2$, C(=NOR$^{11}$)CH(R$^{13}$), CH(R$^{13}$)C(=NOR$^{11}$), $CH_2Z'$, Z'—$CH_2$ and $CH_2Z'CH_2$;

with the proviso that one of Y and Q' is a bond and the other is not a bond;

Z' is selected from C(R$^{11}$)(OR$^{12}$), O, S, C(=O), C(=NOR$^{11}$) and NR$^{11}$;

alternatively, when Q is NR$^2$ and Q' is C(R$^{10}$)$_2$, R$^2$ and one of R$^{10}$ are joined together to form:

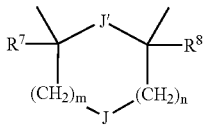

wherein R$^7$ and R$^8$ are each independently selected from H, OH, alkyl, alkoxy, optionally substituted arylalkyl, optionally substituted heteroarylalkyl, $(CH_2)_pOR^{10}$, $(CH_2)_pOC(=O)NR^{11}R^{12}$ and $(CH_2)_pNR^{11}R^{12}$; or R$^7$ and R$^8$ together form a linking group of the formula $CH_2$—$X^3$—$CH_2$;

$X^3$ is a bond, O, S, or NR$^{10}$;

J is selected from a bond, O, CH=CH, S, C(=O), CH(OR$^{10}$), N(R$^{10}$), N(OR$^{10}$), CH(NR$^{11}$R$^{12}$), C(=O)N(R$^{17}$), N(R$^{17}$)C(=O), N(S(O)$_y$R$^9$), N(S(O)$_y$NR$^{11}$R$^{12}$), N(C(=O)R$^{17}$), C(R$^{15}$R$^{16}$), N$^+$(O$^-$)(R$^{10}$), CH(OH)CH(OH) and CH(O(C=O)R$^9$)CH(OC(=O)R$^9$);

J' is selected from O, S, N(R$^{10}$), N$^+$(O$^-$)(R$^{10}$), N(OR$^{10}$) and $CH_2$;

R$^{13}$ is selected from alkyl, aryl and arylalkyl;

R$^{14}$ is the residue of an amino acid after the hydroxyl group of the carboxyl group is removed;

R$^{15}$ and R$^{16}$ are independently selected from H, OH, C(=O)R$^{10}$, O(C=O)R$^9$, alkyl-OH, alkyl, alkoxy and CO$_2$R$^{10}$;

R$^{17}$ is selected from H, alkyl, aryl and heteroaryl;

R$^{22}$ is

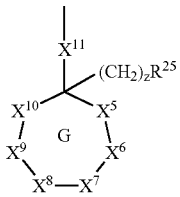

$X^5$ and $X^6$ are independently selected from O, N, S, CHR$^{26}$, C(OH)R$^{26}$, C(=O) and $CH_2$=C;

$X^7$ and $X^8$ are independently selected from a bond, O, N, S, CHR$^{26}$, C(OH)R$^{26}$, C(=O) and $CH_2$=C;

$X^9$ and $X^{10}$ are independently selected from a bond, O, N, S, C(=O) and CHR$^{26}$;

$X^{11}$ is a bond or alkylene optionally substituted with NR$^{11}$R$^{12}$ or OR$^{30}$;

R$^{24}$ is selected from R, thioalkyl, and halogen;

R$^{25}$ is selected from R$^1$ and OC(=O)NR$^{1c}$R$^{1d}$;

R$^{26}$ is selected from H, optionally substituted alkyl and optionally substituted alkoxy, wherein (1) ring G contains 0 to about 3 ring heteroatoms;
(2) any two adjacent hydroxyl groups of ring G can be joined to form a dioxolane ring;
(3) any two adjacent ring carbon atoms of ring G can be joined to form a fused aryl or heteroaryl ring; with the provisos that:
(a) when $X^{11}$ is a bond, ring G can be heteroaryl; and
(b) ring G:
  (i) contains at least one carbon atom that is saturated;
  (ii) does not contain two adjacent ring O atoms;
  (iii) contains a maximum of two C(=O) groups;

R$^{30}$ is selected from H, alkyl, acyl and C(=O)NR$^{11}$R$^{12}$;

m and n are independently selected from 0, 1, and 2;

p is independently selected from 1, 2, 3, and 4;

r is independently selected from 0, 1, and 2;

y is independently selected from 0, 1 and 2; and z is selected from 0, 1, 2, 3 and 4.

In other embodiments, Y is a direct bond and Q is NR$_2$. In other embodiments, B and F is phenyl and Q' is NR$^6$.

In other embodiments, the fused pyrrolocarbazole compound has the following formula (II):

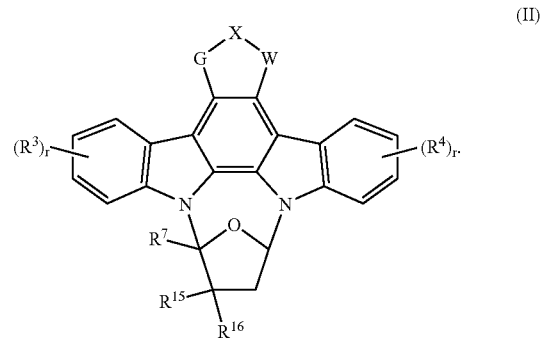

(II)

In other embodiments, G-X-W is selected from $CH_2NR^1C(=O)$, $C(=O)NR^1CH_2$, and $C(=O)NR^1C(=O)$. In other embodiments, R$^3$ and R$^4$ are independently selected from H, alkyl, Cl, Br, $CH_2OH$, $CH_2SOCH_2CH_3$, $CH_2SO_2CH_2CH_3$, $NHCONHC_6H_5$, $CH_2SCH_2CH_3$, $CH_2S$-phenyl, $CH_2S$-pyridyl, CH NHCO$_2$CH$_3$, $CH_2OC(=O)NHCH_2CH_3$, $N(CH_3)_2$, CH=NNH, $CH_2N(CH_3)_2$, and $CH_2OCH_2CH_3$; R$^7$ is selected from H and alkyl; and R$^{15}$ and R$^{16}$ are independently selected from H, alkyl, OH, $CH_2OH$, alkoxy, and CO$_2$alkyl.

In other embodiments, the fused pyrrolocarbazole compound is selected from the formulas (III), (IV), (V), (VIII), and (IX):

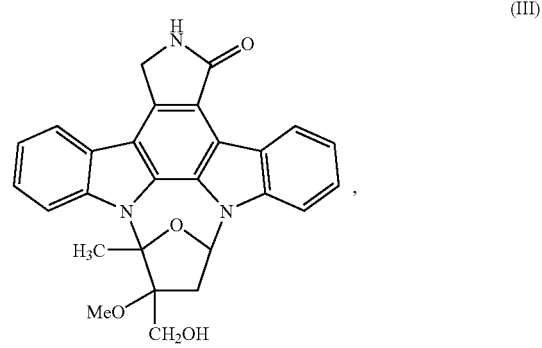

(III)

-continued

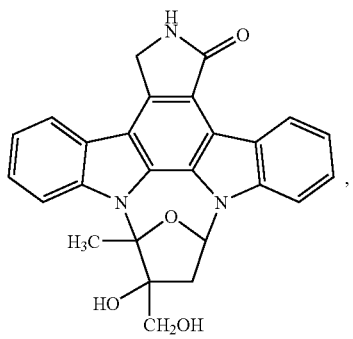
(IV)

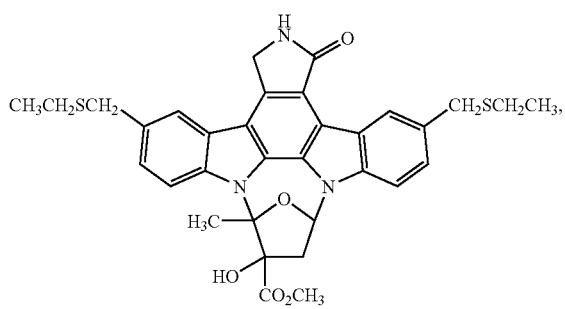
(V)

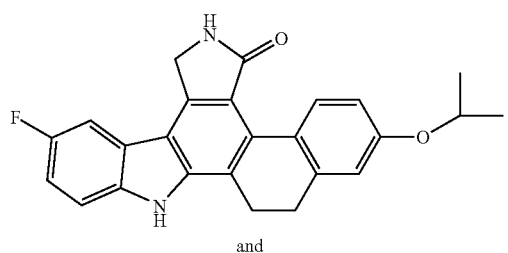
(VIII)

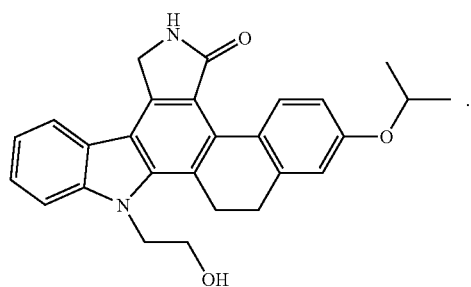
and

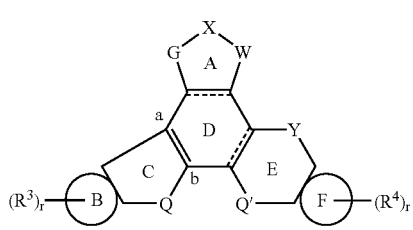
(IX)

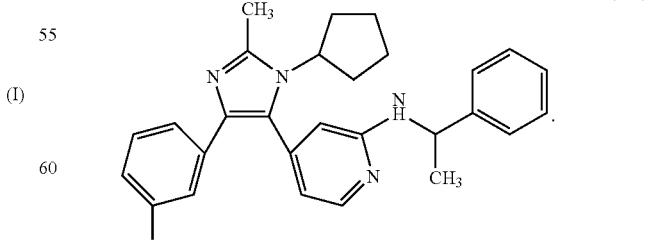
(I)

In other embodiments, the compounds used to treat or prevent pain are stereospecific. For example, in certain preferred embodiments, a fused pyrrolocarbazole has the formula (II-i):

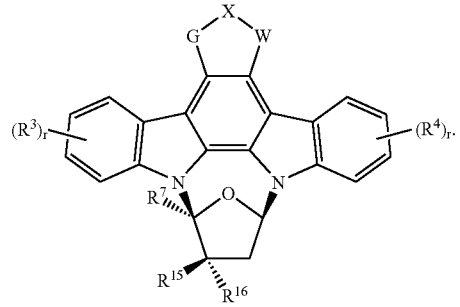
(II-i)

In another embodiment, the present invention provides methods of preventing or treating pain comprising administering to a subject in need thereof an effective amount of a compound having formula (VI):

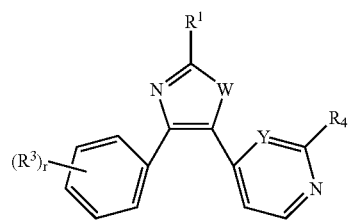
(VI)

wherein:

W is selected from NH, N-alkyl, N-cycloalkyl, N—O-alkyl, and NC(O)alkyl;

Y is C or N;

$R^1$ is alkyl;

$R^3$ is selected from H, halogen, alkyl, CN, and $CF_3$;

$R^4$ is selected from $NH_2$, NH-alkyl, NH-cycloalkyl, NH—O-alkyl, NHC(O)alkyl, NH-aralkyl, and F; and r is selected from 1, 2, and 3.

In certain preferred embodiments, the pain is other than inflammatory pain.

In other embodiments, the compound which prevents or treats pain has formula (VII):

(VII)

In another embodiment, the present invention provides methods of preventing or treating pain comprising administering to a subject in need thereof an effective amount of a compound having formula (X):

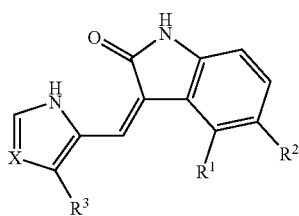

(X)

wherein:

R$^1$ is selected from =—R$^{1a}$, ≡—R$^{1a}$, aryl and heteroaryl, each of which may be substituted by one or more OR$^4$, COR$^4$, COOR$^4$, CONR$^6$R$^7$, NR$^6$R$^7$, NO$_2$, CN, SO$_2$NR$^6$R$^7$, SO$_2$R$^4$, halogen, perfluoroalkyl, lower alkyl, lower alkyl substituted by R$^{1'}$, halogen, cycloalkyl or heterocycle; cycloalkyl or cycloalkyl substituted by R$^{1'}$, halogen, lower alkyl or heterocycle; or heterocycle or heterocycle substituted by R$^{1'}$, lower alkyl or cycloalkyl;

R$^{1a}$ is selected from lower alkyl substituted by R$^{1'}$, aryl, aryloxy, heteroaryl, heteroaryloxy, aryl substituted by R$^{1a'}$, aryloxy substituted by R$^{1a'}$, heteroaryl substituted by R$^{1a'}$, heteroaryloxy substituted by R$^{1a'}$, perfluoroalkyl, cycloalkyl, cycloalkyl substituted by R$^{1'}$ or lower alkyl; heterocycle, and heterocycle substituted by R$^{1'}$ or lower alkyl;

R$^{1'}$ is selected from hydrogen, halogen, OR$^4$, NR$^6$R$^7$, COR$^4$, COOR$^4$, OCOR$^4$, CONR$^6$R$^7$, CN, NO$_2$, SO$_2$R$^4$, and SO$_2$NR$^6$R$^7$;

R$^{1a'}$ is selected from hydrogen, OR$^4$, NR$^6$R$^7$, COR$^4$, COOR$^4$, OCOR$^4$, CONR$^6$R$^7$, CN, NO$_2$, SO$_2$R$^4$, SO$_2$NR$^6$R$^7$, lower alkyl, lower alkyl substituted by R$^{1'}$; cycloalkyl, cycloalkyl substituted by R$^{1'}$; heterocycle, heterocycle substituted by R$^{1'}$; aryl, aryl substituted by R$^{1'}$, perfluoroalkyl, lower alkyl, lower alkyl substituted by R$^{1'}$, cycloalkyl, or cycloalkyl substituted by R$^{1'}$; heterocycle or heterocycle substituted by R$^{1'}$; heteroaryl, and heteroaryl substituted by R$^{1'}$, perfluoroalkyl, lower alkyl, lower alkyl substituted by R$^{1'}$, cycloalkyl, cycloalkyl substituted by R$^{1'}$, heterocycle, or heterocycle substituted by R$^{1'}$;

R$^2$ is selected from hydrogen, OR$^4$, COR$^4$, COOR$^4$, CONR$^6$R$^7$, NR$^6$R$^7$, halogen, NO$_2$, CN, SO$_2$NR$^6$R$^7$, SO$_2$R$^4$, perfluoroalkyl, lower alkyl, and lower alkyl substituted by OR$^8$, NR$^6$R$^7$, COR$^4$, COOR$^4$ or CONR$^6$R$^7$;

R$^3$ is selected from hydrogen, OR$^4$, COR$^4$, OCOR$^4$, COOR$^4$, CONR$^6$R$^7$, NR$^6$R$^7$, halogen, CN, perfluoroalkyl, lower alkyl, and lower alkyl substituted by OR$^8$, NR$^6$R$^7$, COR$^4$, COOR$^4$ or CONR$^6$R$^7$;

R$^4$ is selected from hydrogen, lower alkyl, lower alkyl substituted by R$^{4'}$, cycloalkyl or heterocycle; cycloalkyl or cycloalkyl substituted by R$^{4'}$, lower alkyl or heterocycle; and heterocycle or heterocycle substituted by R$^{4'}$, lower alkyl or cycloalkyl;

R$^{4'}$ is selected from OR$^5$, COOR$^8$, COR$^8$, CONR$^8$R$^9$, NR$^8$R$^9$, CN, NO$_2$, SO$_2$R$^8$, and SO$_2$NR$^8$R$^9$;

R$^5$ is selected from hydrogen, COR$^8$, CONR$^8$R$^9$, lower alkyl or lower alkyl substituted by OR$^9$, NR$^9$R$^{10}$, N(COR$^9$)R$^{10}$, COR$^9$, CONR$^9$R$^{10}$, and COOR$^9$;

R$^6$ and R$^7$ are each independently selected from hydrogen, COR$^8$, COOR$^8$, CONR$^8$R$^9$, SO$_2$R$^8$, SO$_2$NR$^8$R$^9$, lower alkyl, lower alkyl substituted by:
(a) cycloalkyl;
(b) cycloalkyl substituted by R$^{6'}$, lower alkyl or cycloalkyl;
(c) heterocycle;
(d) heterocycle substituted by R$^{6'}$, lower alkyl, or cycloalkyl;
(e) aryl;
(f) aryl substituted by R$^{6'}$, lower alkyl, cycloalkyl, or heterocycle;
(g) heteroaryl;
(h) heteroaryl substituted by R$^{6'}$, lower alkyl, cycloalkyl, or heterocycle;

cycloalkyl, cycloalkyl substituted by R$^{6'}$, lower alkyl or heterocycle; heterocycle, heterocycle substituted by R$^{6'}$, lower alkyl or cycloalkyl; aryl, aryl substituted by R$^{6'}$, lower alkyl, heterocycle or cycloalkyl; heteroaryl, heteroaryl substituted by R$^{6'}$, lower alkyl, heterocycle or cycloalkyl;

alternatively, NR$^6$R$^7$ forms a ring having 3 to 7 atoms, said ring optionally including one or more additional heteroatoms and being optionally substituted by one or more groups selected from lower alkyl, OR$^5$, COR$^8$, COOR$^8$, CONR$^8$R$^9$ and NR$^8$R$^9$;

R$^{6'}$ is selected from OR$^5$, COOR$^8$, COR$^8$, CONR$^8$R$^9$, NR$^8$R$^9$, CN, NO$_2$, SO$_2$R$^8$, and SO$_2$NR$^8$R$^9$;

R$^8$ is selected from hydrogen, lower alkyl, lower alkyl substituted by cycloalkyl, heterocycle, aryl, heteroaryl, OR$^9$, NR$^9$R$^{10}$, or N(COR$^9$)R$^{10}$; aryl, aryl substituted by R$^{8'}$, lower alkyl, cycloalkyl, heterocycle, halogen or SO$_2$F; heteroaryl, heteroaryl substituted by R$^{8'}$, lower alkyl, cycloalkyl, heterocycle, halogen or SO$_2$F; cycloalkyl, cycloalkyl substituted by R$^{8'}$, lower alkyl, heterocycle or aryl; heterocycle, and heterocycle substituted by R$^{8'}$, lower alkyl, cycloalkyl or aryl;

R$^{8'}$ is selected from OR$^9$, COOR$^9$, COR$^9$, CONR$^9$R$^{10}$, NR$^{10}$R$^9$, CN, NO$_2$, SO$_2$R$^9$, and SO$_2$NR$^{10}$R$^9$;

R$^9$ and R$^{10}$ are each independently selected from hydrogen, lower alkyl and aryl; and X is selected from N and CH.

In certain preferred embodiments, the pain is other than inflammatory pain. In certain preferred embodiments, R$^8$ is selected from hydrogen, lower alkyl, lower alkyl substituted by cycloalkyl, heterocycle, aryl, heteroaryl, OR$^9$, NR$^9$R$^{10}$, and N(COR$^9$)R$^{10}$; aryl, aryl substituted by R$^{8'}$, lower alkyl, cycloalkyl or heterocycle; heteroaryl, heteroaryl substituted by R$^{8'}$, lower alkyl, cycloalkyl, heterocycle; cycloalkyl, cycloalkyl substituted by R$^{8'}$, lower alkyl, heterocycle or aryl; heterocycle, and heterocycle substituted by R$^{8'}$, lower alkyl, cycloalkyl or aryl; and R$^9$ and R$^{10}$ are each independently selected from hydrogen, lower alkyl.

In certain preferred embodiments, the compound of formula (X) is:

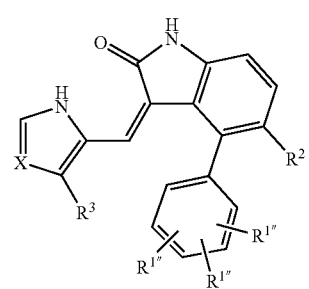

(X)

wherein R$^{1''}$ is selected from hydrogen, OR$^4$, COR$^4$, COOR$^4$, CONR$^6$R$^7$, NR$^6$R$^7$, NO$_2$, CN, SO$_2$NR$^6$R$^7$, SO$_2$R$^4$, halogen, perfluoroalkyl, lower alkyl, lower alkyl substituted by R$^{1'}$, halogen, cycloalkyl or heterocycle; cycloalkyl or cycloalkyl substituted by $R^{1'}$, halogen, lower alkyl or heterocycle; and heterocycle or heterocycle substituted by $R^{1'}$, halogen, lower alkyl or cycloalkyl.

In certain preferred embodiments, $R^2$ is selected from hydrogen, $OR^4$, $COOR^4$, $CONR^6R^7$, $NR^6R^7$, $NO_2$, perfluoroalkyl, halogen, lower alkyl, and lower alkyl substituted by $OR^8$ or $NR^6R^7$. In certain preferred embodiments, $R^3$ is selected from hydrogen, $OR^4$, $NR^6R^7$, lower alkyl, and lower alkyl substituted by $OR^8$ and $NR^6R^7$. In certain preferred embodiments, $R^4$ is selected from hydrogen, lower alkyl, lower alkyl substituted by $OR^5$, $COOR^8$, $COR^8$, $NR^8R^9$, and $CONR^8R^9$. In certain preferred embodiments, $R^5$ is selected from hydrogen, $COR^8$, $CONR^8R^9$, and lower alkyl. In certain preferred embodiments, $R^6$ and $R^7$ are each independently selected from hydrogen, $COR^8$, $COOR^8$, $CONR^8R^9$, $SO_2R^8$, aryl, heteroaryl, lower alkyl, and lower alkyl substituted by $OR^5$ and $NR^8R^9$. In certain preferred embodiments, $R^{1a}$ is lower alkyl substituted by phenyl substituted by one to three substituents selected from hydroxy, lower alkoxy, di-(lower alkyl)-amino, di-(lower alkyl)-amino-lower alkoxy, morpholino-lower alkyl, carboxy-lower alkoxy and lower alkanoylamino.

In another embodiment, the present invention provides methods of preventing or treating pain comprising administering to a patient an effective amount of a compound having formula (XI):

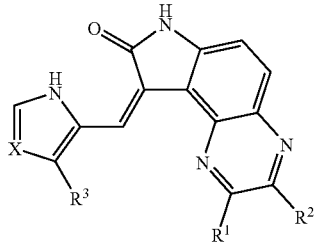

(XI)

wherein:
$R^1$ and $R^2$ are independently selected from hydrogen, $OR^4$, $COR^4$, $COOR^4$, $CONR^6R^7$, $NR^6R^7$, lower alkyl optionally substituted by:
(a) $R^{1'}$, wherein $R^{1'}$ is selected from halogen, $OR^4$, $NR^6R^7$, $COR^4$, $COOR^4$, $OCOR^4$, $CONR^6R^7$, CN, $SO_2R^4$, and $SO_2NR^6R^7$;
(b) cycloalkyl optionally substituted by $R^{11}$;
(c) heterocycle optionally substituted by $R^{11}$;
(d) aryl optionally substituted by $R^{12}$;
(e) heteroaryl optionally substituted by $R^{12}$;
cycloalkyl optionally substituted by:
(a) $R^{1'}$;
(b) lower alkyl optionally substituted by $R^{11}$;
(c) heterocycle optionally substituted by $R^{11}$;
(d) aryl optionally substituted by $R^{12}$;
(e) heteroaryl optionally substituted by $R^{12}$,
heterocycle optionally substituted by:
(a) $R^{1'}$;
(b) lower alkyl optionally substituted by $R^{11}$;
(c) cycloalkyl optionally substituted by $R^{11}$;
(d) aryl optionally substituted by $R^{12}$;
(e) heteroaryl optionally substituted by $R^{12}$;
aryl optionally substituted by:
(a) $R^{1''}$, wherein $R^{1''}$ is selected from halogen, $OR^4$, $NR^6R^7$, halogen, $NO_2$, perfluoroalkyl, $COR^4$, $COOR^4$, $OCOR^4$, $CONR^6R^7$, CN, $SO_2R^4$, and $SO_2NR^6R^7$;
(b) lower alkyl optionally substituted by $R^{11}$;
(c) cycloalkyl optionally substituted by $R^{11}$;
(d) heterocycle optionally substituted by $R^{11}$;
(e) aryl optionally substituted by $R^{12}$;
(f) heteroaryl optionally substituted by $R^{12}$;
heteroaryl optionally substituted by
(a) $R^{1'''}$;
(b) lower alkyl optionally substituted by $R^{11}$;
(c) cycloalkyl optionally substituted by $R^{11}$;
(d) heterocycle optionally substituted by $R^{11}$;
(e) aryl optionally substituted by $R^{12}$;
(f) heteroaryl optionally substituted by $R^{12}$;
alternatively, $R^1$ and $R^2$ join to form a ring having 5–7 atoms, said ring optionally including one or more heteroatoms and being optionally substituted by a member of the group consisting of $OR^8$, $COR^7$, $COOR^7$, $OCOR^4$, $CONR^7R^9$, $NR^8R^9$, or lower alkyl which may be substituted by the group $R^{11}$;

$R^3$ is selected from hydrogen, $OR^4$, $COR^4$, $OCOR^4$, $COOR^4$, $CONR^6R^7$, $NR^6R^7$, halogen, CN, perfluoroalkyl, lower alkyl, and lower alkyl substituted by $OR^4$, $OCOR^4$ or $NR^5R^6$;

$R^4$ is selected from hydrogen, lower alkyl optionally substituted by:
(a) $R^{4'}$, wherein $R^{4'}$ is selected from $OR^8$, $COR^7$, $COOR^7$, $CONR^5R^6$, $NR^5R^6$, $SO_2R^7$, $SO_2NR^5R^6$;
(b) cycloalkyl optionally substituted by $R^{11}$;
(c) heterocycle optionally substituted by $R^{11}$;
(d) aryl optionally substituted by $R^{12}$;
(e) heteroaryl optionally substituted by $R^{12}$;
cycloalkyl optionally substituted by:
(a) $R^{4'}$;
(b) lower alkyl optionally substituted by $R^{11}$;
(c) heterocycle optionally substituted by $R^{11}$;
(d) aryl optionally substituted by $R^{12}$;
(e) heteroaryl optionally substituted by $R^{12}$;
heterocycle optionally substituted by:
(a) $R^{4'}$;
(b) lower alkyl optionally substituted by $R^{11}$;
(c) cycloalkyl optionally substituted by $R^{11}$;
(d) aryl optionally substituted by $R^{12}$;
(e) heteroaryl optionally substituted by $R^{12}$;
aryl optionally substituted by:
(a) $R^{4''}$, wherein $R^{4''}$ is selected from halogen, $OR^8$, $NR^5R^6$, halogen, $NO_2$, perfluoroalkyl, $COR^7$, $COOR^7$, $CONR^5R^6$, $SO_2R^7$, and $SO_2NR^5R^6$;
(b) lower alkyl optionally substituted by $R^{11}$;
(c) cycloalkyl optionally substituted by $R^{11}$;
(d) heterocycle optionally substituted by $R^{11}$;
(e) aryl optionally substituted by $R^{12}$;
(f) heteroaryl optionally substituted by $R^{12}$;
heteroaryl optionally substituted by
(a) $R^{4'''}$;
(b) lower alkl optionally substituted by $R^{11}$;
(c) cycloalkyl optionally substituted by $R^{11}$;
(d) heterocycle optionally substituted by $R^{11}$;
(e) aryl optionally substituted by $R^{12}$;
(f) heteroaryl optionally substituted by $R^{12}$;

$R^5$ and $R^6$ are each independently selected from hydrogen, $COR^7$, $COOR^7$, $CONR^7R^9$, lower alkyl optionally substituted by:
(a) $R^{5'}$, wherein $R^{5'}$ is selected from halogen, $OR^8$, $NR^7R^8$, $COR^7$, $COOR^7$, $CONR^7R^8$, $SO_2R^7$, and $SO_2NR^7R^8$;
(b) cycloalkyl optionally substituted by $R^{11}$;
(c) heterocycle optionally substituted by $R^{11}$;
(d) aryl optionally substituted by $R^{12}$;
(e) heteroaryl optionally substituted by $R^{12}$;

cycloalkyl optionally substituted by:
  (a) $R^{5"}$;
  (b) lower alkyl optionally substituted by $R^{11}$;
  (c) heterocycle optionally substituted by $R^{11}$;
  (d) aryl optionally substituted by $R^{12}$;
  (e) heteroaryl optionally substituted by $R^{12}$;
heterocycle optionally substituted by:
  (a) $R^{5"}$;
  (b) lower alkyl optionally substituted by $R^{11}$;
  (c) cycloalkyl optionally substituted by $R^{11}$;
  (d) aryl optionally substituted by $R^{12}$;
  (e) heteroaryl optionally substituted by $R^{12}$;
aryl optionally substituted by:
  (a) $R^{4"}$, wherein $R^{4"}$ is selected from halogen, $OR^8$, $NR^7R^8$, halogen, $NO_2$, perfluoroalkyl, $COR^7$, $COOR^7$, $CONR^7R^8$, $SO_2R^7$, and $SO_2NR^7R^8$;
  (b) lower alkyl optionally substituted by $R^{11}$;
  (c) cycloalkyl optionally substituted by $R^{11}$;
  (d) heterocycle optionally substituted by $R^{11}$;
  (e) aryl optionally substituted by $R^{12}$;
  (f) heteroaryl optionally substituted by $R^{12}$;
heteroaryl optionally substituted by
  (a) $R^{4"}$;
  (b) lower alkyl optionally substituted by $R^{11}$;
  (c) cycloalkyl optionally substituted by $R^{11}$;
  (d) heterocycle optionally substituted by $R^{11}$;
  (e) aryl optionally substituted by $R^{12}$;
  (f) heteroaryl optionally substituted by $R^{12}$;
alternatively, $R^5$ and $R^6$ join to form a ring having 3–7 atoms, said ring optionally including one or more additional heteroatoms and being optionally substituted by lower alkyl, $OR^8$, $COR^7$, $COOR^7$, $CONR^7R^9$ or $NR^8R^9$;

$R^7$ is selected from hydrogen or lower alkyl optionally substituted by a group selected from cycloalkyl, heterocycle, aryl, heteroaryl, $OR^9$ and $NR^8R^9$;

$R^8$ is selected from hydrogen, $COR^9$, $CONR^9R^{10}$ and lower alkyl optionally substituted by $R^{11}$;

$R^9$ and $R^{10}$ are each independently selected from hydrogen or lower alkyl;

$R^{11}$ is selected from $OR^9$, $COR^9$, $COOR^9$, $OCOR^9$, $CONR^9R^{10}$, $NR^9R^{10}$, $N(COR^9)R^{10}$, $SO_2R^9$, and $SO_2NR^9R^{10}$;

$R^{12}$ is selected from $OR^9$, $COR^9$, $COOR^9$, $OCOR^9$, $CONR^9R^{10}$, $NR^9R^{10}$, $N(COR^9)R^{10}$, $SO_2R^9$, $SO_2NR^9R^{10}$, halogen, CN, $NO_2$ or perfluoroalkyl; and X is selected from N and CH;

In certain preferred embodiments, the pain is other than inflammatory pain. In certain preferred embodiments, $R^1$ and $R^2$ are independently selected from hydrogen, $NR^6R^7$, and substituted lower alkyl. In certain preferred embodiments, $R^3$ is selected from hydrogen, $OR^4$, $NR^6R^7$, and lower alkyl substituted by $OR^4$ or $NR^5R^6$.

In another embodiment, the present invention provides methods of preventing or treating pain comprising administering to a subject in need thereof an effective amount of a compound having formula (XII) or (XIII):

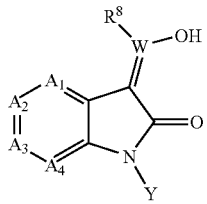
(XII)

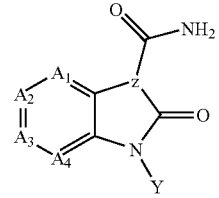
(XIII)

wherein:
Y is selected from $(CH_2)Q_1$, $CO-Q_1$, $CONHQ_1$, $COO-Q_1$, $SO_2Q_1$, and $SO_2NHQ_1$;

$Q_1$ is selected from lower alkyl, lower alkenyl, a 5–7 membered aromatic or non-aromatic carbocyclic or heterocyclic ring, a 9–14 membered bicyclic or tricyclic aromatic or non-aromatic carbocyclic or heterocyclic ring, wherein the alkyl, alkenyl, ring or ring system is optionally substituted with one to four substituents, each of which is independently selected from $NH_2$, NHR, $N(R)_2$, $NO_2$, OH, OR, $CF_3$, halogen, CN, $CO_2H$, $CONH_2$, CONHR, $CON(R)_2$, COR, SR, S(O)R, $SO_2R$, $SO_2NHR$, and R;

W is selected from C and N wherein when W is N, $R^8$ is a lone pair of electrons;

$A_1$ is selected from N and $CR^1$;
$A_2$ is selected from N and $CR^2$;
$A_3$ is selected from N and $CR^3$;
$A_4$ is selected from N and $CR^4$; provided that at least one of $A_1$, $A_2$, $A_3$, and $A_4$ is other than N;

$R^1$ is selected from $NHR^5$, $OR^5$, $SR^5$, and $R^5$;

$R^2$, $R^3$, and $R^4$ are independently selected from $CONH_2$, CONHR, $CON(R)_2$, $NHR^5$, $NHCH_2R^5$, $OR^5$, $SR^5$, $R^5$, $NHCOR6$, $NHCONHR^6$, $NHCONHCOR^6$, $NHCOOR^6$, $NHSO_2R^6$, $NHSO_2NHR^6$, COOH, COOR, $COQ_1$, $CONHQ_1$, $CONRQ_1$, $COOQ_1$, $SO_2Q_1$, and $SO_2NHQ_1$;

$R^5$ and $R^6$ are each independently selected from hydrogen, $N(R)_2$, NHOH, $NO_2$, COOR, halogen, lower alkyl, lower alkenyl, lower alkynyl, a 5–7 membered aromatic or non-aromatic carbocyclic or heterocyclic ring, a 9–14 membered bicyclic or tricyclic aromatic or non-aromatic carbocyclic or heterocyclic ring, wherein the alkyl, alkenyl, ring or ring system is optionally substituted with one to four substituents, each of which is independently selected from $NH_2$, NHR, NHCOOR, $N(R)_2$, $NO_2$, OH, OR, $CF_3$, halogen, CN, $Si(R)_3$, $CO_2H$, COOR, $CONH_2$, CONHR, $CON(R)_2$, COR, SR, S(O)R, $SO_2R$, $SO_2NHR$, and R;

$R^7$ is selected from hydrogen, lower alkyl, lower alkenyl, a 5–7 membered aromatic or non-aromatic carbocyclic or heterocyclic ring, and a 9–14 membered bicyclic or tricyclic aromatic or non-aromatic carbocyclic or heterocyclic ring, wherein the alkyl, alkenyl, ring or ring system is optionally substituted with one to four substituents, each of which is independently selected from $NH_2$, NHR, $N(R)_2$, $NO_2$, OH, OR, $CF_3$, halogen, CN, $CO_2H$, $CONH_2$, CONHR, $CON(R)_2$, COR, SR, S(O)R, $SO_2R$, $SO_2NHR$, and R;

R is selected from lower alkyl, lower alkenyl, a 5–7 membered aromatic or non-aromatic carbocyclic or heterocyclic ring, and a 9–10 membered bicyclic aromatic or non-aromatic carbocyclic or heterocyclic ring system; and z is selected from CH and N.

In certain preferred embodiments, the pain is other than inflammatory pain. In certain preferred embodiments, Y is $(CH_2)Q_1$ and $Q_1$ is substituted phenyl.

In another embodiment, the present invention provides methods of preventing or treating pain comprising administering to a subject in need thereof an effective amount of a compound having formula (XIV):

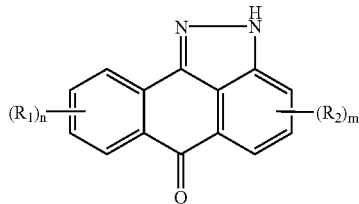
(XIV)

or a pharmaceutically acceptable salt thereof; wherein:

R$_1$ and R$_2$ are optional substituents that are the same or different and independently represent alkyl, halogen, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono- or di-alkylaminoalkoxy, or a group represented by formula (a), (b), (c) or (d):

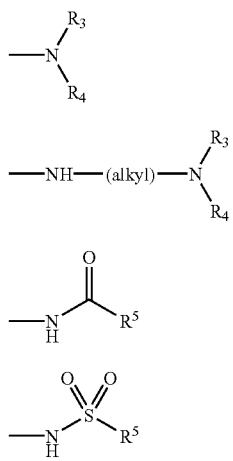

(a)

(b)

(c)

(d)

R$_3$ and R$_4$ taken together represent alkylidene or a heteroatom-containing alkylidene, or R$_3$ and R$_4$ are the same or different and independently represent hydrogen, alkyl, cycloalkyl, aryl, arylalkyl, cycloalkylalkyl, aryloxyalkyl, alkoxyalkyl, alkoxyamino, or alkoxy(mono- or di-alkylamino);

R$^5$ represents hydrogen, alkyl, cycloalkyl, aryl, arylalkyl, cycloalkylalkyl, alkoxy, amino, mono- or di-alkylamino, arylamino, arylalkylamino, cycloalkylamino, or cycloalkylalkylamino; and m and n are independently 0 1, or 2, with the proviso that at least R$_1$ or R$_2$ is present.

In certain preferred embodiments, the compound has the formula (XIV-i) or (XIV-ii):

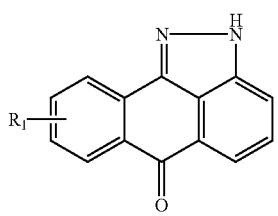
(XIV-i)

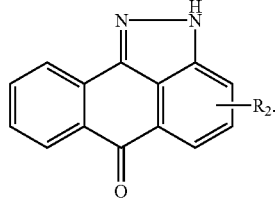
(XIV-ii)

In certain preferred embodiments, the compound has the formula (XIV-i), (XIV-ii) or (XIV-iii):

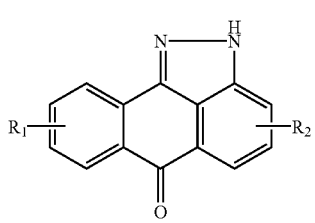
(XIV-iii)

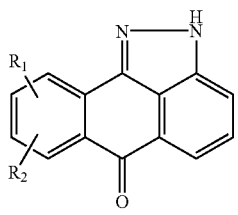
(XIV-iv)

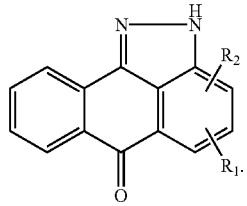
(XIV-v)

In certain preferred embodiments, the pain is other than inflammatory pain.

In other embodiments, the present invention provides a method of treating or preventing pain comprising administering to a subject in need thereof an effective amount of a compound selected from stress-activated protein kinase inhibitors. In other embodiments, the compound inhibits a substrate involved in the stress-activated protein kinase pathway selected from JNK1, JNK2, and JNK3. In other embodiments, the compounds described herein are administered to the subject sufficiently prior to a painful stimulus to modulate, particularly decrease, the painful event. In other embodiments, the invention relates to methods of preventing or treating pain wherein the pain is other than inflammatory pain.

A wide variety of SAPK inhibitors are available which may be suitable for use in the methods of the present invention. Generally speaking, it is only necessary that the compounds provide the desired effect (for example, pain prevention and/or alleviation), and be capable of being employed in the present methods, as discussed in detail below. Methods of treating or preventing disorders include, but are not limited to, treating or preventing those pathological and neurological disorders associated with pain, wherein the treatment or prevention comprises inhibiting the activity thereof by contacting the receptor with an active drug substance. In certain embodiments, the present methods may involve SAPK inhibitors which are the particular compounds described herein, or are derivatives thereof.

As used herein, the term "stress-activated protein kinase (SAPK)", means a subfamily of proteins involved in the signal transduction machinery, through which signals may be transduced from the cell surface to the nucleus in response to different stimuli. This course of events is understood to proceed, inter alia, through phosphorylation of intracellular substrates such as other protein kinases and transcription factors. The SAPK protein may be any protein identified as belonging to the SAPK class of proteins. Preferably, the SAPK protein is selected from the group consisting of p54 SAPKα/β/JNK2 and p45 SAPKγ/JNK1 and the p38 MAPKs (α, β, βII, γ, and δ) which are described above. In certain preferred embodiments of the invention, the present methods involve compounds including, for example, the compounds described herein (or derivatives thereof) which may be capable of interacting or binding with and/or inhibiting SAPK proteins as determined, for example, by binding assays, kinase assays, or other equivalent assays.

As used herein, the terms "inhibit" and "inhibition" mean that the activity of proteins, for example, SAPK, is diminished, reduced or suppressed in the presence of natural, synthetic or semi-synthetic molecules.

Compounds (including, for example, fused pyrrolocarbazole compounds) that may be employed in the methods of the present invention (i.e., compounds which inhibit SAPK activity), may be identified using procedures which would be apparent to one of ordinary skill in the art, once armed with the teachings of the present application. For example, compounds may be contacted with a cell or cells containing SAPK. This may be carried out in suitable buffers or media which are well known to those skilled in the art. Alternatively, compounds may be contacted with a cell or cells containing SAPK in vivo. Using these procedures, compounds which inhibit the activity of SAPK may be readily identified. In this connection, SAPK activity can be determined using a number of techniques. For example, SAPK activity may be determined, for example, by measuring the activity of a substrate of SAPK. Such substrates have been reported in the literature and may be readily discernable to those skilled in the art. Generally speaking, the substrate may be a member of the mitogen activated protein kinase family or other substrates involved in the pathway including, for example, a protein selected from JNK1, JNK2, JNK3, ERK1, ERK2, p38α, p38β, p38γ, p38δ, MEK1, MEK2, MKK3, MKK4 (SEK1), MEK5, MKK6, MKK7, jun, ATF2, ELK1, MLK1, MLK2, MLK3, MLK4, and the mammalian homolog of AEX-3, and also general substrates of Ser/Thr protein kinases such as myelin basic protein (MBP). In certain preferred embodiments, the substrate is selected from JNK1, JNK2, and JNK3.

Reagents and methods for measuring the activity of the substrates are also known to those skilled in the art. The presence of SAPK can also be determined by measuring the amount of the SAPK or mRNA encoding the SAPK. Reagents, including antibodies and oligonucleotide probes, as well as methods of measuring the amount of DNA or protein, including Northern and Western blots, are well known to those skilled in the art. SAPK activity can also be determined by an in vitro kinase assay. In vitro kinase assays are well known to those skilled in the art and may be employed to identify suitable compounds for use in the methods of the present invention.

The ability of SAPK inhibitors to prevent and/or treat pain may be evaluated using procedures which are well known to a person of ordinary skill in the art. As used herein, the term "pain" means a physiologic and/or psychologic reaction or response to potential or actual stimulus that may result in tissue damage, injury or disease, which shows considerable complexity and subjectivity when compared with other sensory systems. Generally speaking, the SAPK inhibitor may be administered to a patient in vivo, for example, prior to, during or after a stimulus which may cause pain or discomfort to the patient. In preferred embodiments, the SAPK inhibitor is administered to a patient in vivo prior to the painful stimulus. Also, preferably, the SAPK inhibitor may be administered to the patient in vivo sufficiently prior to the painful stimulus to enable the inhibitor to decrease the painful event including, for example, preventing and/or treating pain before, or immediately upon, the painful stimulus. By way of general guidance, the SAPK inhibitor may be administered to a subject about 48 hours before the onset of pain. Preferably, the SAPK inhibitor may be administered to a subject from about 1 minute to about 24 hours before the onset of pain. More preferably, the SAPK inhibitor is administered about 2 hours to about 24 hours before the onset of pain. The pain relieving effect of the compound may be evaluated, for example, based on its ability to suppress the pain event resulting from the stimulus.

Broadly speaking, "fused pyrrolocarbazole" means a compound having the following general core structure:

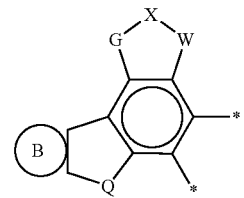

wherein at least one of G, X, or W is a nitrogen, B is an aryl or heteroaryl group, Q is nitrogen, oxygen or an optionally substituted methylene group, and * indicates the attachment point of an additional fused ring system.

The core structures provided herein are presented by way of general guidance, and are not to be taken as limiting the scope of the invention. For example, certain cores may indicate the presence of certain atoms for illustrative purposes. It will be appreciated that such atoms may be bonded to additional groups, or may be further substituted without deviating from the spirit of the invention.

Thus, fused pyrrolocarbazole core structures include, but are not limited to, structures of formula IA:

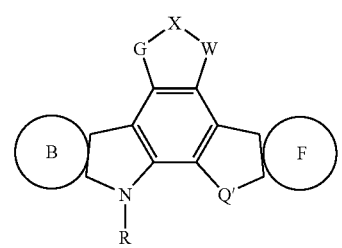

IA wherein Q' may be a moiety containing one or more nitrogens or carbons. Such structures may include, but are not limited to, indolocarbazoles, indenocarbazoles, and bridged indenocarbazoles.

As used herein, "indolocarbazole" may indicate a compound of formula IA, wherein Q and Q' are nitrogens and Y is a bond:

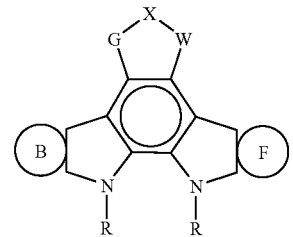

These compounds may include, but are not limited to, structures in which the nitrogens of the carbazole and the indole form a cyclic bridged moiety:

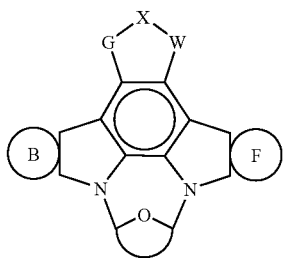

Such bridged structures may include, but are not limited to, derivatives of the microbial-derived material referred to as K-252a.

As used herein, "indenocarbazole" may indicate a compound of formula IA in which Q is other than nitrogen. These compounds may include, but are not limited to, compounds wherein Q is one or more carbons. For example, in certain indenocarbazoles, Q may be a single carbon:

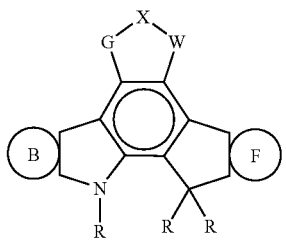

As used herein, "bridged indenopyrrolocarbazole" may indicate a compound of formula Ia in which Q is a moiety containing at least one carbon which joins with the nitrogen of the carbazole derivative to form a bridged moiety:

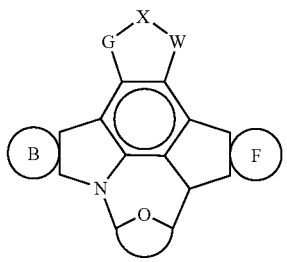

As used herein, "isomeric fused indolocarbazole" may indicate a compound of formula I in which Q' is a direct bond. These isomeric fused pyrrolocarbazole compounds may be represented by the formula:

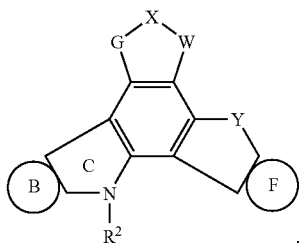

Fused pyrrolocarbazoles which may be represented by the foregoing compounds and which may be employed in the methods of the present invention are disclosed, for example, in U.S. Pat. Nos. 4,923,986; 4,877,776; 5,093,330; 5,461,146; 5,468,872; 5,621,100; 5,621,101; 5,516,771; 5,475,110; 5,591,855; 5,594,009; 5,705,511; 5,616,724; 5,801,190; and 5,599,808; PCT publication Nos. WO 93/08809 and WO 97/46565; U.S. application Ser. No. 09/325,140, filed Jun. 4, 1999; U.S. provisional application Ser. No. 60/119,834, filed Feb. 12, 1999; and U.S. provisional application Ser. No. 60/150,367, filed Aug. 20, 1999, the disclosures of each of which are hereby incorporated herein by reference, in their entireties.

In preferred embodiments, the compounds employed in the methods of the present invention may be stable compounds. As used herein, "stable compound" or "stable structure" may indicate a compound that is sufficiently robust to survive isolation to a useful degree of purity from a reaction mixture, and preferably capable of formulation into an efficacious therapeutic agent.

The fused pyrrolocarbazoles may be further substituted. As used herein, "substituted" indicates that one or more hydrogen atoms on the indicated atom may be replaced with a selected group referred to herein as a "substituent", provided that the substituted atom's valency is not exceeded, and that the substitution may result in a stable compound.

As used herein, the term "alkyl" means a straight-chain, cyclic, or branched alkyl group having 1 to about 8 carbon atoms, such as methyl, ethyl, propyl, isopropyl, butyl, isobutyl, sec-butyl, tert-butyl, pentyl, isoamyl, neopentyl, 1-ethylpropyl, hexyl, octyl, cyclopropyl, and cyclopentyl. The alkyl moiety of alkyl-containing groups, such as alkoxy, alkoxycarbonyl, and alkylaminocarbonyl groups, has the same meaning as alkyl defined above. Lower alkyl groups, which are preferred, are alkyl groups as defined above which contain 1 to about 4 carbons.

Alkyl groups and alkyl moieties contained within substituent groups such as aralkyl, alkoxy, arylalkoxy, hydroxyalkoxy, alkoxy-alkoxy, hydroxy-alkylthio, alkoxyalkylthio, alkylcarbonyloxy, hydroxyalkyl and acyloxy groups may be optionally substituted (i.e., substituted or unsubstituted). A substituted alkyl group has 1 to about 3 independently-selected substituents, preferably hydroxy, lower alkoxy, lower alkoxy-alkoxy, arylalkoxy-lower alkoxy, heteroarylalkoxy-lower alkoxy, arylalkoxy, heterocycloalkoxy, halogen, carboxyl, lower alkoxycarbonyl, nitro, amino, mono- or di-lower alkylamino, dioxolane, dioxane, dithiolane, dithione, furan, lactone, or lactam.

As used herein, the term "alkenyl" means straight-chain, cyclic, or branched hydrocarbon chains having at least one carbon-carbon double bond. Examples of alkenyl groups include ethenyl, propenyl, 3-methylbutenyl, and cyclohexenyl groups. As used herein, the term "alkynyl" means straight-chain, cyclic, or branched hydrocarbon chains having at least one carbon-carbon triple bond. Examples of alkynyl groups include ethynyl, propynyl, 3-methylbutynyl, and cyclohexynyl groups.

As used herein, the "acyl" moiety of acyl-containing groups such as acyloxy groups includes a straight-chain, branched, or cyclic alkanoyl group having 1 to about 6 carbon atoms, such as formyl, acetyl, propanoyl, butyryl, valeryl, pivaloyl or hexanoyl.

As used herein, the term "carbocyclic" means cyclic groups in which the ring portion is composed solely of carbon atoms. These include, but are not limited to, carbocyclic groups having from about 3 to about 12 carbons. Exemplary carbocyclic groups include, for example, cyclopropyl, cyclobutyl, cyclopentyl, cyclohexl, cycloheptyl, cyclooctyl. The term "carbocyclic aromatic ring" includes carbocyclic rings which are also aryl rings. The terms "heterocyclo" and "heterocyclic" refer to cyclic groups in which the ring portion includes from about 2 to about 9 carbon atoms and at least one heteroatom such as O, N, or S. Heterocyclyl groups include heteroaryl and heteroalkyl groups.

As used herein, the term "aryl" means an aromatic ring having from about 6 to about 12 carbon atoms such as phenyl, biphenyl and naphthyl. Preferred aryl groups include unsubstituted or substituted phenyl and naphthyl groups. The term "heteroaryl" as used herein denotes an aryl group in which one or more ring carbon atoms is replaced by a hetero (i.e., non-carbon) atom such as O, N or S. Preferred heteroaryl groups include pyridyl, pyrimidyl, pyrrolyl, furyl, thienyl, imidazolyl, triazolyl, tetrazolyl, quinolyl, isoquinolyl, benzoimidazolyl, thiazolyl, pyrazolyl, and benzothiazolyl groups. The term "heteroalkyl" denotes a cycloalkyl group in which one or more ring carbon atoms is replaced by hetero atoms such as O, N, or S.

As used herein, the term "aralkyl" (or "arylalkyl") denotes a group having from about 7 to about 15 carbons, consisting of an alkyl group that bears an aryl group. Examples of aralkyl groups include, but are not limited to, benzyl, phenethyl, benzhydryl and naphthylmethyl groups. Substituted aryl, substituted heterocyclic and substituted aralkyl groups each have 1 to about 3 independently selected substituents that are preferably lower alkyl, hydroxy, lower alkoxy, carboxy, lower alkoxycarbonyl, nitro, amino, mono- or di-lower alkylamino, and halogen.

Preferred heterocyclic groups formed with a nitrogen atom include, for example, pyrrolidinyl, piperidinyl, piperidino, morpholinyl, morpholino, thiomorpholino, N-methylpiperazinyl, indolyl, isoindolyl, imidazole, imidazoline, oxazoline, oxazole, triazole, thiazoline, thiazole, isothiazole, thiadiazoles, triazines, isoxazole, oxindole, indoxyl, pyrazole, pyrazolone, pyrimidine, pyrazine, quinoline, iosquinoline, and tetrazole groups. Preferred heterocyclic groups formed with an oxygen atom include, for example, furan, tetrahydrofuran, pyran, benzofurans, isobenzofurans, and tetrahydropyran groups. Preferred heterocyclic groups formed with a sulfur atom include, for example, thiophene, thianaphthene, tetrahydrothiophene, tetrahydrothiapyran, and benzothiophenes.

As used herein, "hydroxyalkyl" groups are alkyl groups that have a hydroxyl group appended thereto. As used herein, "hydroxyalkoxy" groups are alkoxy groups that have a hydroxyl group appended thereto. As used herein, "halogen" refers to fluorine, chlorine, bromine and iodine.

As used herein, the term "heteroarylalkyl" means an arylalkyl group that contains a heteroatom in the aryl moiety. The term "oxy" denotes the presence of an oxygen atom. Thus, "alkoxy" groups are alkyl groups that are attached through an oxygen atom, and "carbonyloxy" groups are carbonyl groups that are attached through an oxygen atom.

As used herein, the terms "heterocycloalkyl" and "heterocycloalkoxy" mean an alkyl or an alkoxy group that has a heterocyclo group attached to the alkyl moiety thereof, and the term "arylalkoxy" means an alkoxy group that has an aryl group attached to the alkyl moiety thereof. As used herein, the term "alkylcarbonyloxy" means a group of formula —O—C(=O)-alkyl.

As used herein, the term "alkyloxy-alkoxy" means an alkoxy group that contains an alkyloxy substituent attached to its alkyl moiety. The term "alkoxy-alkylthio" means an alkylthio group (i.e., a group of formula —S-alkyl) that contains an alkoxy substituent attached to its alkyl moiety. The term "hydroxy-alkylthio" means an alkylthio group (i.e., a group of formula —S-alkyl) that contains a hydroxy substituent attached to its alkyl moiety.

As used herein, the term "monosaccharide" has its accustomed meaning as a simple sugar. As used herein, the term "amino acid" means a molecule containing both an amino group and a carboxyl group. Embodiments of amino acids include α-amino acids; i.e., carboxylic acids of general formula HOOC—CH(NH$_2$)-(side chain). Side chains of amino acids include naturally occurring and non-naturally occurring moieties. Non-naturally occurring (i.e., unnatural) amino acid side chains are moieties that are used in place of naturally occurring amino acid side chains in, for example, amino acid analogs. See, e.g., Lehninger, *Biochemistry*, Second Edition, Worth Publishers, Inc, 1975, pages 73–75, the disclosures of which are hereby incorporated herein by reference in their entirety. In certain embodiments, substituent groups for the compounds described herein include the residue of an amino acid after removal of the hydroxyl moiety of the carboxyl group thereof, i.e., groups having the formula —C(=O)CH(NH$_2$)-(side chain).

In preferred embodiments, the compounds employed in the present methods are preferably employed in an effective amount. As used herein, an "effective amount" refers to an amount of compound which prevents or treats pain, preferably pain associated with pathological or neurological disorders.

The compounds employed in the present methods may be present in various forms as will be appreciated by the skilled artisan. Such forms include, but are not limited to, pharmaceutically acceptable salts, prodrugs, polymorphs, stereoisomers, and the like. As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ration.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two.

Generally, nonaqueous media like ether, ethyl acetate, ethanol, isopropanol, or acetonitrile are preferred. Lists of suitable salts are disclosed in *Remington's Pharmaceutical Sciences,* 17th ed., Mack Publishing Company, Easton, Pa., 1985, p. 1418, the disclosures of which are hereby incorporated herein by reference, in their entirety.

In preferred form, the methods of the present invention may involve administering to a subject an effective amount of a fused pyrrolocarbazole compound having formula (I). Other fused pyrrolocarbazole compounds which may be employed in the methods of the present invention, as well as methods for their preparation, would be readily apparent to one of ordinary skill in the art, once armed with the teachings of the present disclosure.

In other preferred forms, the method of the present invention involves administering to a subject an effective amount of a compound of formula (VI). Methods for the preparation of compounds of formula (VI) will be readily apparent to one of ordinary skill in the art and are exemplified in International Publication WO 00/06563, filed Jul. 27, 1999, the disclosure of which is hereby incorporated by reference in its entirety.

In other preferred forms, the method of the present invention involves administering to a subject an effective amount of a compound of formula (X). Methods for the preparation of compounds of formula (X) will be readily apparent to one of ordinary skill in the art and are exemplified in International Publication WO 00/35909, filed Jun. 22, 2000, and International Publication WO 00/35906, filed Jun. 22, 2000, the disclosures of which are hereby incorporated by reference in their entirety.

In other preferred forms, the method of the present invention involves administering to a subject an effective amount of a compound of formula (XI). Methods for the preparation of compounds of formula (XI) will be readily apparent to one of ordinary skill in the art and are exemplified in International Publication WO 00/35921, filed Jun. 22, 2000, the disclosure of which is hereby incorporated by reference in its entirety.

In other preferred forms, the method of the present invention involves administering to a subject an effective amount of a compound of formula (XII) or (XIII). Methods for the preparation of compounds of formula (XII) and (XIII) will be readily apparent to one of ordinary skill in the art and are exemplified in International Publication WO 00/64872, filed Nov. 2, 2000, the disclosure of which is hereby incorporated by reference in its entirety.

In other preferred forms, the method of the present invention involves administering to a subject an effective amount of a compound of formula (XIV). Methods for the preparation of compounds of formula (XIV) will be readily apparent to one of ordinary skill in the art and are exemplified in International Publication WO 01/12609 A1, filed Aug. 19, 2000, the disclosure of which is hereby incorporated by reference in its entirety.

In certain preferred embodiments, the compounds described herein are used to treat or prevent pain which is other than inflammatory pain.

The compounds employed in the methods of the present invention may exist in prodrug form. As used herein, "prodrug" is intended to include any covalently bonded carriers which release the active parent drug, for example, as according to formulas (I) or other formulas or compounds employed in the methods of the present invention in vivo when such prodrug is administered to a mammalian subject. Since prodrugs are known to enhance numerous desirable qualities of pharmaceuticals (e.g., solubility, bioavailability, manufacturing, etc.) the compounds employed in the present methods may, if desired, be delivered in prodrug form. Thus, the present invention contemplates methods of delivering prodrugs. Prodrugs of the compounds employed in the present invention, for example formula (I), may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

The compounds of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. In this connection, the fused pyrrolocarbazoles may be epimeric derivatives of K-252a as described in U.S. Pat. No. 6,093,713, the disclosure of which is hereby incorporated by reference. A preferred fused pyrrolocarbazole has the stereochemistry indicated below wherein G, X, W, $R^3$, $R^4$, $R^7$, $R^{15}$, $R^{16}$, and r are defined herein.

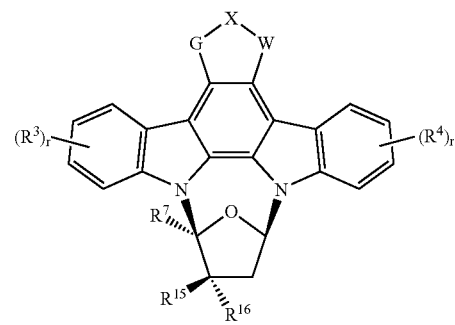

It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

As will be readily understood, functional groups present may contain protecting groups during the course of synthesis. For example, the amino acid side chain substituents of the compounds of Formula Ia can be substituted with protecting groups such as benzyloxycarbonyl. Protecting groups are known per se as chemical functional groups that can be selectively appended to and removed from functionalities, such as amine, hydroxyl, and carboxyl groups. These groups are present in a chemical compound to render such functionality inert to chemical reaction conditions to which the compound is exposed. Any of a variety of protecting groups may be employed with the present invention. Preferred protecting groups include the benzyloxycarbonyl (Cbz) group and the tert-butyloxycarbonyl (Boc) group. Other preferred protecting groups according to the invention may be found in Greene, T. W. and Wuts, P. G. M., *Protective Groups in Organic Synthesis* 2d. Ed., Wiley & Sons, 1991.

Fused pyrrolocarbazoles, such as indolocarbazoles may be synthesized by methods taught, for example, in U.S. Pat. Nos. 4,923,986; 4,877,776; 5,093,330; 5,461,146; 5,468,872; 5,621,100; 5,621,101; 5,516,771; and 5,599,808; and PCT publication Nos. WO 93/08809 and WO 97/46565, the disclosures of which are hereby incorporated herein by reference, in their entireties. Additional methods of preparation are set forth in Moody et al., *J. Org. Chem.* 57:2105–2114 (1992), the disclosures of which are hereby incorporated herein by reference, in their entirety.

Fused pyrrolocarbazoles, such as indenocarbazoles, as well as additional compounds wherein Q is not a single nitrogen, may be synthesized by methods taught, for example, in U.S. Pat. Nos. 5,475,110; 5,591,855; 5,594,009; 5,705,511; 5,616,724; and 5,801,190; the disclosures of which are hereby incorporated herein by reference in their entirety.

Fused pyrrolocarbazoles, such as bridged indenocarbazoles, may be prepared by methods taught, for example, in U.S. application Ser. No. 09/325,140, filed Jun. 4, 1999, the disclosures of which are hereby incorporated herein by reference in its entirety.

Cyclic substituted fused pyrrolocarbazoles and isoindolones may be prepared by methods taught, for example, in U.S. provisional application Ser. No. 60/119,834, filed Feb. 12, 1999, the disclosures of which are hereby incorporated herein by reference in its entirety.

Isomeric fused indolocarbazoles may be prepared by methods taught, for example, in U.S. provisional application Ser. No. 60/150,367, filed Aug. 20, 1999, the disclosures of which are hereby incorporated herein by reference in its entirety.

The compounds employed in the methods of the present invention including, for example, fused pyrrolocarbazole compounds, may be administered by any means that results in the contact of the active agents with the agents' site or site(s) of action in the body of a patient. As used herein, the term "subject" refers to animals, including mammals, preferably humans. The compounds may be administered by any conventional means available for use in conjunction with pharmaceuticals, either as individual therapeutic agents or in a combination of therapeutic agents. For example, they may be administered as the sole active agents in a pharmaceutical composition, or they can be used in combination with other therapeutically active ingredients.

The compounds are preferably combined with a pharmaceutical carrier selected on the basis of the chosen route of administration and standard pharmaceutical practice as described, for example, in *Remington's Pharmaceutical Sciences* (Mack Pub. Co., Easton, Pa., 1980), the disclosures of which are hereby incorporated herein by reference, in their entirety. Accordingly, it will be appreciated that the present invention includes the preparation of a medicament for use in the treatment of pain as described herein.

Compounds of the present invention can be administered to a mammalian host in a variety of forms adapted to the chosen route of administration, e.g., orally or parenterally. Parenteral administration in this respect includes administration by the following routes: intravenous, intramuscular, subcutaneous, rectal, intraocular, intrasynovial, transepithelial including transdermal, ophthalmic, sublingual and buccal; topically including ophthalmic, dermal, ocular, rectal, and nasal inhalation via insufflation aerosol.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. By way of general guidance, suitable compositions may be those formulated by blending an active ingredient with a polymer, sugar and other ingredients, dissolving the blend, and freeze-drying the solution as described in *Manuf. Chemist.*, 36, 1990, pp. 36–37, the disclosure of which is hereby incorporated by reference.

Compositions and preparations should preferably contain at least 0.1% of active compound. The percentage of the compositions and preparations may, of course, be varied and may conveniently be, for example, from about 2 to about 6% of the weight of the unit including all combinations and sub-combinations therein. The amount of active compound in such therapeutically useful compositions is preferably such that a suitable dosage will be obtained. Preferred compositions or preparations according to the present invention may be prepared so that an oral dosage unit form contains from about 0.1 to about 1000 mg of active compound, preferably about 25 to about 100 mg of active compound, more preferably about 40 to about 80 mg of active compound.

The tablets, troches, pills, capsules and the like may also contain one or more of the following: a binder, such as gum tragacanth, acacia, corn starch or gelatin; an excipient, such as dicalcium phosphate; a disintegrating agent, such as corn starch, potato starch, alginic acid and the like; a lubricant, such as magnesium stearate; a sweetening agent such as sucrose, lactose or saccharin; or a flavoring agent, such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. Of course, any material used in preparing any dosage unit form is preferably pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or a pharmacologically acceptable salt can be prepared in water suitably mixed with a surfactant, such as hydroxypropylcellulose. A dispersion can also be prepared in glycerol, liquid polyethylene glycols and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the active compound in the required amount, in the appropriate solvent, with various of the other ingredients enumerated above, as required, followed by filtered sterilization. Generally, dispersions may be prepared by incorporating the sterilized active ingredient into a sterile vehicle that contains the basic dispersion medium and the required other ingredients from those enumerated above. In the case of sterile powders for the preparation of sterile injectable solutions, the preferred methods of preparation may include vacuum drying and the freeze drying technique which yield a powder of the active ingredient, plus any additional desired ingredient from the previously sterile-filtered solution thereof.

The therapeutic compounds of this invention may be administered to a subject alone or in combination with a pharmaceutically acceptable carrier. As noted above, the relative proportions of active ingredient and carrier may be determined, for example, by the solubility and chemical nature of the compound, chosen route of administration and standard pharmaceutical practice.

The dosage of the compounds of the present invention that will be most suitable for prophylaxis or treatment will vary with the form of administration, the particular compound chosen and the physiological characteristics of the particular subject under treatment. Generally, small dosages may be used initially and, if necessary, increased by small increments until the desired effect under the circumstances is reached. The therapeutic human dosage, based on physiological studies using rats, may generally range from about 0.01 mg to about 100 mg/kg of body weight per day, and all combinations and sub-combinations of ranges therein. The therapeutic human dosage may be from about 0.4 mg to about 10 g or higher, and may be administered in several different dosage units and forms from once to several times a day. Preferably, the human dosage is about 50 mg/kg administered orally or subcutaneously. As will be appreciated by those of skill in the art, doses in humans may be higher or lower depending upon various physiological differences. Generally speaking, oral administration may require higher dosages.

EXAMPLES

The invention is further demonstrated in the following examples. All of the examples are actual examples. The examples are for purposes of illustration and are not intended to limit the scope of the present invention.

The examples which follow employ a formalin-induced behavioral response model. In this model, the intraplantar administration of 50 µl 5% formalin into the hindpaw of the rat produces a very clearly defined set of behaviors in the animal which are indicative of pain. The two behavioral responses measured are flinching/shaking of the hindquarters and licking/biting of the injected paw. This model is also characterized by its biphasic effect, as demonstrated in FIGS. 1 to 8. This biphasic phase is characterized by a short duration phase I response which lasts 10 to 15 minutes, followed by a quiescent period (5 to 10 minutes), followed by a more robust phase II response. This model has been characterized in several species and is sensitive to the analgesic effects of compounds such as NSAIDs, morphine and codeine, administered by a variety of routes, including local administration directly into the paw.

Figure 11:
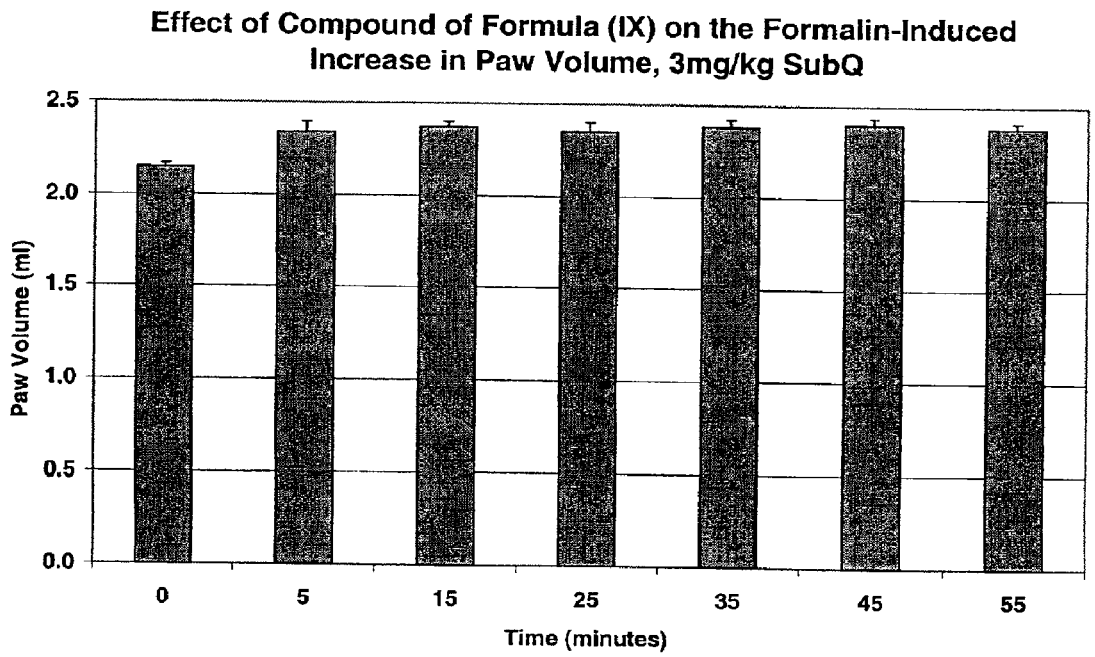

The formalin model is a model of non-acute pain in which phase I is a localized response in the hindpaw and phase II is a centrally mediated behavior. The phase II response also corresponds to "wind-up" or central sensitization. The compounds described herein may be used to treat or prevent pain which is other than inflammatory pain. In such instances, the following model may be used to determine the effect of the compounds on inflammation. The injection of formalin into the hind paw of a rat, as described above, produces an to inflammation of the hind paw that can be measured with a plethysmometer. The increase in paw volume is about 0.25 mL or an increase in paw volume of about 13% (see, for example, FIG. 9). Pretreatment of rats with compounds VIII and IX at doses that inhibit phase II of the formalin behavioral response had no effect upon the inflammation produced formalin. (see, for example, FIGS. 10 and 11). The present invention may be further understood by reference to the following examples.

Example 1

The compound of formula (V) was administered subcutaneously at doses of 1.0 mg/kg in 30% Solutol™ (BASF Corp., Parsippany, N.J.), 24 hours prior to the formalin challenge. This experiment was repeated twice employing four animals per experiment. During the experiments, formalin-induced behavioral effects characterized as flinching/shaking (see FIGS. 1 and 3) and licking/biting were observed (see FIGS. 2 and 4).

As depicted graphically in FIGS. 1 to 4, the compound of formula (V) demonstrated activity for the prevention and/or treatment of pain according to the formalin model. Specifically, FIGS. 1 and 3 show that the compound of formula (V) resulted in a decrease in the flinching/shaking responses of about 15% in phase I and about 30% in phase II. FIGS. 2 and 4 show that the compound of formula (V) resulted in a decrease in licking/biting responses of about 10% in phase I and about 25 to 30% in phase II.

Example 2

The compound of formula (V) was administered subcutaneously at doses of 1.0 mg/kg in 30% Solutol™, 2 hours prior to the formalin challenge. This experiment was also repeated twice with four animals per experiment. During the experiments, formalin-induced behavioral effects characterized as flinching/shaking (FIG. 5) and licking/biting were observed (FIG. 6). In these experiments, the compound of formula (V) did not substantially inhibit the formalin-induced behavioral effects.

Example 3

The compound of formula (V) was administered subcutaneously in rats, at doses of 0.3, 1.0 and 3.0 mg/kg, in 30% Solutol™, 24 hours prior to challenge with formalin. The inhibitory effects of the varying dosages of the compound of formula (V) on formalin-induced behavioral effects was observed and are depicted graphically in FIGS. 7 and 8. As set forth in FIGS. 7 and 8, the inhibitory response to formalin induction by the compound of formula (V) is dose-dependent. Specifically, increasing the dosage of the compound of formula (V) administered to the rat from 0.3 mg/kg to 3.0 mg/kg (i.e., a 10-fold increase) resulted in a substantial improvement in the inhibition of formalin-induced behavioral effects in phases I and II. No substantial difference in inhibition was observed between the dosages of 1.0 and 3.0 mg/kg.

The present invention may be further understood by reference to Table 1, which provides inhibition of Phase II of the formalin response by certain compounds of the present invention when administered subcutaneously two hours prior to formalin administration.

| Compound | % Inhibition of Phase II | Dose mg/kg |
|---|---|---|
| 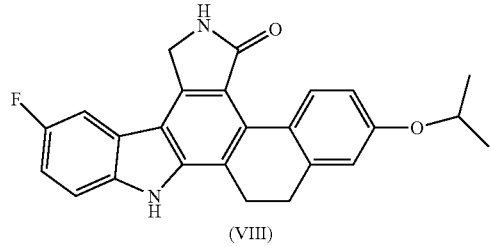 (VIII) | 29 ± 4 | 1 |
| 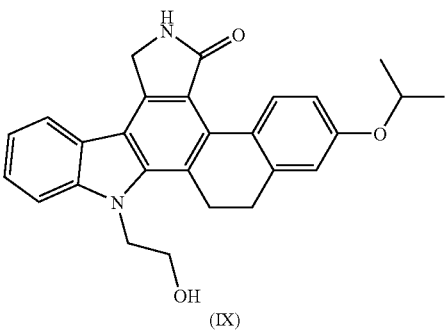 (IX) | 37 ± 3 | 3 |
| 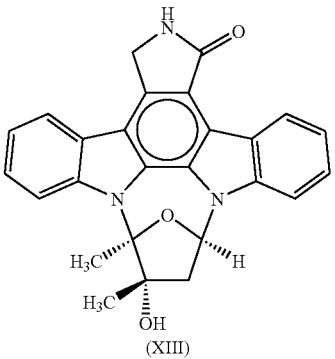 (XIII) | 29 ± 5 | 3 |
| 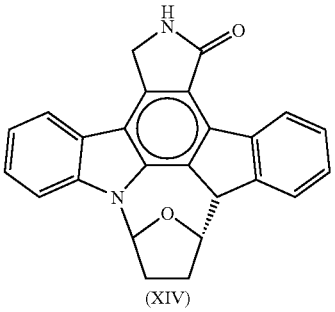 (XIV) | 34 ± 3 | 3 |

-continued

| Compound | % Inhibition of Phase II | Dose mg/kg |
|---|---|---|
| 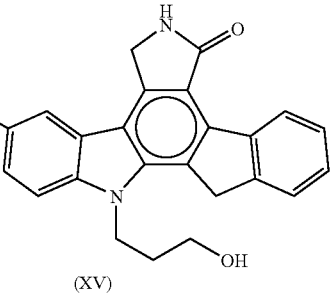 (XV) | 19 ± 3 | 10 |
| 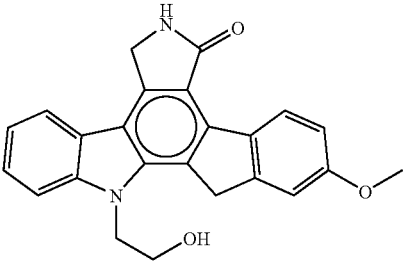 (XVI) | 22 ± 6 | 3 |

The disclosures of each patent, patent application and publication cited or described in this document are hereby incorporated herein by reference, in their entirety. Various modifications of the invention, in addition to those described herein, will be apparent to those skilled in the art from the foregoing description. Such modifications are also intended to fall within the scope of the appended claims.

What is claimed is:

1. A method of treating pain in a subject in need thereof comprising administering to the subject an effective amount of a compound having the following Formula II:

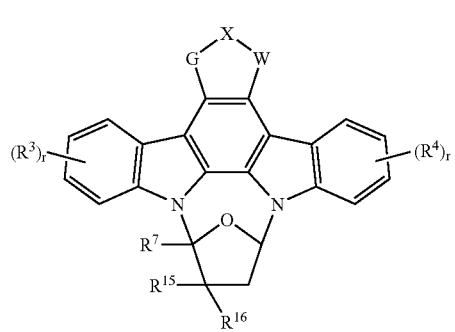

or a stereoisomer or pharmaceutically acceptable salt form thereof, wherein:

G-X-W is selected from:
(a) $(Z^1Z^2)C-N(R^1)-C(Z^1Z^2)$;
(b) $CH(R^1)-C(=O)-N(R^1)$; and
(c) $N(R^1)-C(=O)-CH(R^1)$;

$Z^1$ and $Z^2$, at each occurrence, are independently selected from H, H; H, OR; H, SR; H, $N(R)_2$; and a group wherein $Z^1$ and $Z^2$ together form a moiety selected from =O, =S, and =NR; with the proviso that at least one of the pairs $Z^1$ and $Z^2$ forms =O;

R is independently selected from H, optionally substituted alkyl, $C(=O)R^{1a}$, $C(=O)NR^{1c}R^{1d}$, $(CH_2)_pNR^{1c}R^{1d}$, $(CH_2)_pOR^{1b}$, optionally substituted arylalkyl and optionally substituted heteroarylalkyl;

$R^1$ is independently selected from:
(a) H, optionally substituted alkyl, optionally substituted aryl, optionally substituted arylalkyl, optionally substituted heteroaryl and optionally substituted heteroarylalkyl;
(b) $C(=O)R^{1a}$;
(c) $OR^{1b}$;
(d) $C(=O)NHR^{1b}$, $NR^{1c}R^{1d}$, $(CH_2)_pNR^{1c}R^{1d}$, $(CH_2)_pOR^{1b}$, $O(CH_2)_pOR^{1b}$ and $O(CH_2)_pNR^{1c}R^{1d}$;

$R^{1a}$ is independently selected from optionally substituted alkyl, optionally substituted aryl and optionally substituted heteroaryl;

$R^{1b}$ is independently selected from H and optionally substituted alkyl;

$R^{1c}$ and $R^{1d}$ are each independently selected from H and optionally substituted alkyl, or together form linking group of the formula $(CH_2)_2-X^1-(CH_2)_2$;

$R^3$ and $R^4$ are each independently selected from:
(a) H, aryl, heteroaryl, F, Cl, Br, I, CN, $CF_3$, $NO_2$, OH, $OR^9$, $O(CH_2)_pNR^{11}R^{12}$, $OC(=O)R^9$, $OC(=O)NR^{11}R^{12}$, $O(CH_2)_pOR^{10}$, $CH_2OR^{10}$, $NR^{11}R^{12}$, $NR^{10}S(=O)_2R^9$ and $NR^{10}C(=O)R^9$;
(b) $CH_2OR^{14}$;
(c) $NR^{10}C(=O)NR^{11}R^{12}$, $CO_2R^{10}$, $C(=O)R^9$, $C(=O)NR^{11}R^{12}$, $CH=NOR^{10}$, $CH=NR^{10}$, $(CH_2)_pNR^{11}R^{12}$, $(CH_2)_pNHR^{14}$ and $CH=NNR^{11}R^{12}$;
(d) $S(O)_yR^9$, $(CH_2)_pS(O)_yR^9$ and $CH_2S(O)_yR^{14}$;
(e) optionally substituted alkyl, optionally substituted alkenyl and optionally substituted alkynyl, wherein said optional substituents are one to about three $R^5$ groups;

$R^5$ is selected from aryl, heteroaryl, arylalkoxy, F, Cl, Br, I, CN, $NO_2$, OH, $OR^9$, $OC(=O)R^9$, $OC(=O)NHR^{10}$, O-tetrahydropyranyl, $NR^{11}R^{12}$, $NR^{10}C(=O)R^9$, $NR^{10}CO_2R^9$, $NR^{10}C(=O)NR^{11}R^{12}$, $NHC(=NH)NH_2$, $NR^{10}S(O)_2R^9$, $S(O)_yR^9$, $CO_2R^{10}$, $C(=O)NR^{11}R^{12}$, $C(=O)R^9$, $CH_2OR^{10}$, $CH=NNR^{11}R^{12}$, $CH=NOR^{10}$, $CH=NR^9$, $CH=NNHCH(N=NH)NH_2$, $S(=O)_2NR^{11}R^{12}$, $P(=O)(OR^{10})_2$, $OR^{14}$, and a monosaccharide wherein each hydroxyl group of the monosaccharide is independently either unsubstituted or is replaced by H, alkyl, alkylcarbonyloxy, or alkoxy;

$R^7$ is selected from H, OH, alkyl, alkoxy, optionally substituted arylalkyl, optionally substituted heteroarylalkyl, $(CH_2)_pOR^{10}$, $(CH_2)_pOC(=O)NR^{11}R^{12}$ and $(CH_2)_pNR^{11}R^{12}$;

$R^9$ is selected from alkyl, $(CH_2)_r$aryl and $(CH_2)_r$heteroaryl;

$R^{10}$ is selected from H, alkyl, $(CH_2)_r$aryl and $(CH_2)_r$heteroaryl;

$R^{11}$ and $R^{12}$ are independently selected from H and optionally substituted alkyl, or together form a linking group of the formula $(CH_2)_2-X^1-(CH_2)_2$;

$X^1$ is independantly selected from O, S and $CH_2$;

$R^{14}$ is the residue of an amino acid after the hydroxyl group of the carboxyl group is removed;

$R^{15}$ and $R^{16}$ are independently selected from H, OH, $C(=O)R^{10}$, $O(C=O)R^9$, alkyl-OH, alkyl, alkoxy and $CO_2R^{10}$;

p is independently selected from 1, 2, 3, and 4;

r is independently selected from 0, 1, and 2; and y is independently selected from 0, 1 and 2.

2. The method according to claim 1 wherein G-X-W is selected from $CH_2NR^1C(=O)$, $C(=O)NR^1CH_2$, and $C(=O)NR^1C(=O)$.

3. The method according to claim 2 wherein $R^1$ is H, $R^3$ and $R^4$ are independently selected from H, alkyl, Cl, Br, $CH_2OH$, $CH_2SOCH_2CH_3$, $CH_2SO_2CH_2CH_3$, $NHCONHC_6H_5$, $CH_2SCH_2CH_3$, $CH_2S$-phenyl, $CH_2S$-pyridyl, $CH_2NHCO_2CH_3$, $CH_2OC(=O)NHCH_2CH_3$, $N(CH_3)_2$, $CH=NNH$, $CH_2N(CH_3)_2$, and $CH_2OCH_2CH_3$; $R^7$ is selected from H and alkyl; and $R^{15}$ and $R^{16}$ are independently selected from H, alkyl, OH, $CH_2OH$, alkoxy, and $CO_2$alkyl.

4. The method according to claim 1 wherein the compound is selected from Formulas (III), (IV), (V):

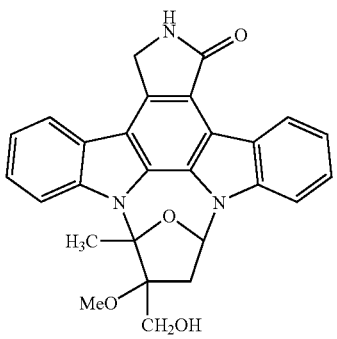

(III)

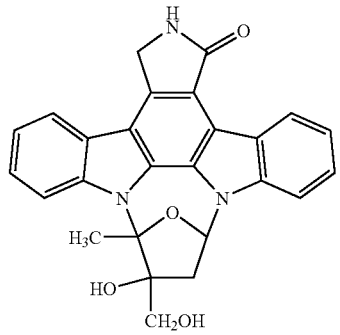

(IV)

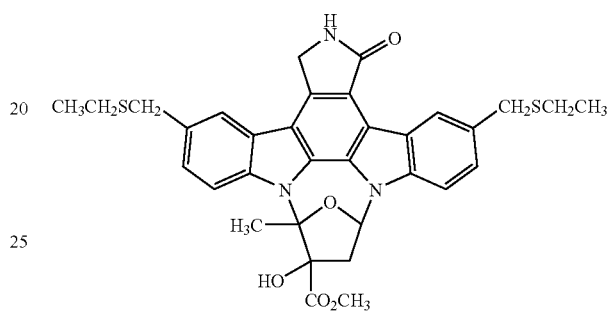

(V)

or a stereoisomer or pharmaceutically acceptable salt form thereof.

5. The method according to claim 1 wherein the fused pyrrolocarbazole compound has formula (II-i):

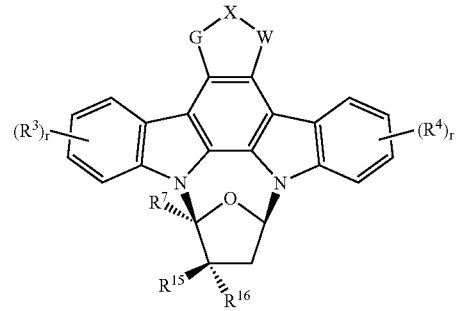

(II-i)

or a stereoisomer or pharmaceutically acceptable salt form thereof.

6. The method according to claim 5 wherein G is $CH_2$, X is NH, W is C=O, and r is 1.

7. The method according to claim 5 wherein G-X-W is selected from $CH_2NR^1C(=O)$, $C(=O)NR^1CH_2$, and $C(=O)NR^1C(=O)$.

8. The method according to claim 5 wherein $R^1$ is H, $R^3$ and $R^4$ are independently selected from H, alkyl, Cl, Br, $CH_2OH$, $CH_2SOCH_2CH_3$, $CH_2SO_2CH_2CH_3$, $NHCONHC_6H_5$, $CH_2SCH_2CH_3$, $CH_2S$-phenyl, $CH_2S$-pyridyl, $CH_2NHCO_2CH_3$, $CH_2OC(=O)NHCH_2CH_3$, $N(CH_3)_2$, $CH=NNH$, $CH_2N(CH_3)_2$, and $CH_2OCH_2CH_3$; $R^7$ is selected from H and alkyl; and $R^{15}$ and $R^{16}$ are independently selected from H, alkyl, OH, $CH_2OH$, alkoxy, and $CO_2$alkyl.

9. The method according to claim 5 wherein the compound has Formula (V-i):

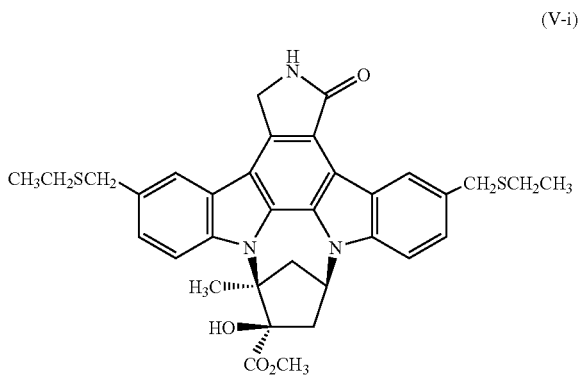

(V-i)

or a stereoisomer or pharmaceutically acceptable salt form thereof.

10. The method according to claim 1 wherein the compound is administered to the subject sufficiently prior to the onset of pain.

11. The method according to claim 10 wherein the compound is administered to the subject about 1 minute to about 48 hours prior to the onset of pain.

12. The method according to claim 11 wherein the compound is administered to the subject about 1 hour to about 24 hours prior to the onset of pain.

13. The method according to claim 1 wherein the pain is other than inflammatory pain.

14. The method according to claim 9 wherein the compound is administered to the subject sufficiently prior to the onset of pain.

15. The method according to claim 9 wherein the compound is administered to the subject about 1 minute to about 48 hours before the onset of pain.

16. The method according to claim 9 wherein the compound is administered to the subject about 1 hour to about 24 hours before the onset of pain.

17. The method according to claim 9 wherein the pain is other than inflammatory pain.

* * * * *